United States Patent
Umeda et al.

(10) Patent No.: US 7,422,750 B2
(45) Date of Patent: Sep. 9, 2008

(54) FOOD OR BEVERAGE CONTAINING FUCOIDAN AND METHOD OF PRODUCTION THEREOF

(75) Inventors: Yoshihisa Umeda, Mie (JP); Hiroshi Kihara, Otsu (JP); Katsushige Ikai, Otsu (JP); Ikunoshin Kato, Otsu (JP)

(73) Assignee: Takara Bio Inc., Shiga-Ken (JP)

( * ) Notice: Subject to any disclaimer, the term of this patent is extended or adjusted under 35 U.S.C. 154(b) by 518 days.

(21) Appl. No.: 10/408,346

(22) Filed: Apr. 8, 2003

(65) Prior Publication Data

US 2005/0049221 A1    Mar. 3, 2005

Related U.S. Application Data

(63) Continuation of application No. 09/987,715, filed on Nov. 15, 2001, now Pat. No. 6,573,250, which is a continuation of application No. 09/180,465, filed as application No. PCT/JP97/01664 on May 15, 1997, now abandoned.

(30) Foreign Application Priority Data

| Jun. 12, 1996 | (JP) | ................................. 96/171666 |
| Nov. 15, 1996 | (JP) | ................................. 96/318598 |

(51) Int. Cl.
    *A61K 36/02*    (2006.01)
(52) U.S. Cl. ..................... 424/195.17; 426/658; 514/54
(58) Field of Classification Search ............. 435/257.1; 424/195.17; 426/615; 536/128
    See application file for complete search history.

(56) References Cited

U.S. PATENT DOCUMENTS

| 1,814,981 | A | * | 7/1931 | Thornley et al. ................ 536/3 |
| 2,128,551 | A | * | 8/1938 | Le Gloahce et al. ............ 536/3 |
| 2,188,092 | A | * | 1/1940 | Le Gloahec et al. ......... 536/128 |
| 2,624,727 | A | * | 1/1953 | Le Gloahec ................. 536/128 |
| 3,175,942 | A |   | 3/1965 | Anderson et al. ............. 514/54 |
| 3,502,483 | A | * | 3/1970 | Klose et al. .................. 426/575 |
| 3,998,974 | A |   | 12/1976 | Zaffaroni .................... 426/534 |
| 5,192,566 | A |   | 3/1993 | Cox et al. ..................... 428/89 |
| 5,861,048 | A |   | 1/1999 | Kamasaka ...................... 71/11 |
| 6,207,652 | B1 |   | 3/2001 | Sakai et al. .................... 514/54 |

FOREIGN PATENT DOCUMENTS

| EP | 0 645 143 A1 |   | 3/1995 |
| JP | 56-026174 |   | 3/1981 |
| JP | 56-085269 |   | 7/1981 |
| JP | 62-179368 | * | 8/1987 |
| JP | 1-87601 |   | 3/1989 |
| JP | 5-49491 |   | 3/1995 |
| JP | 7-138166 |   | 5/1995 |
| JP | 7-215990 |   | 8/1995 |
| JP | 7-228603 | * | 8/1995 |
| JP | 8-196234 |   | 8/1996 |
| JP | 9-40574 |   | 2/1997 |

OTHER PUBLICATIONS

T. Usui et al., "Isolation of Highly Purified Fucoidan from *Eisenia bicyclis* and its Anticoagulant and Antitumor Activities", Agric. Biol. Chem., vol. 44, No. 8, pp. 1965-1966, 1980.
Whistler et al., "Polysaccharide Chemistry", Academic Press, New York, pp. 355-356, 1953.
Chemical Abstracts 111(3): 17459q (1989).
Chemical Abstracts 121(19): 226391g (1994).
Chemical Abstracts 116(21): 207491v (1992).

* cited by examiner

*Primary Examiner*—Susan C Hoffman
(74) *Attorney, Agent, or Firm*—Wenderoth, Lind & Ponack, L.L.P.

(57) ABSTRACT

Food or beverage where fucoidan which is derived from a fucoidan-containing substance is contained therein, added thereto and/or diluted therein. Food or beverage where fucoidan which is derived from a fucoidan-containing substance and where algins are reduced or eliminated, is contained therein. Apoptosis-inducing food or beverage where an effective amount of fucoidan having an apoptosis-inducing ability is contained therein.

7 Claims, 5 Drawing Sheets

FOOD OR BEVERAGE CONTAINING FUCOIDAN AND METHOD OF PRODUCTION THEREOF

This application is a continuation of Ser. No. 09/987,715, filed Nov. 15, 2001, now U.S. Pat. No. 6,573,250, which is a continuation of Ser. No. 09/180,465, filed Nov. 9, 1998, which has now been abandoned, which is a 371 of PCT/JP97/01664, filed May 15, 1997.

BACKGROUND OF THE INVENTION

1. Field of the Invention

The present invention relates to food or beverage which contains fucoidan and has an excellent physiological effect as well.

2. Description of the Related Art

Fucoidan is a polysaccharide containing sulfated fucose which is contained in seaweed, trepang, etc. No attempt for researching and developing fucoidan and for positively using it in food and beverage has been known yet.

The object of the present invention is to offer fucoidan-containing materials, and to offer fucoidan-containing food and beverage having a physiological activity which is useful for good health and having an excellent taste.

SUMMARY OF THE INVENTION

The present invention will be summarized as follows. The first feature of the present invention relates to food or beverage which contains fucoidan derived from fucoidan-containing substances.

The second feature of the present invention relates to food or beverage which contains fucoidan wherein algins derived from the fucoidan-containing substances are reduced or removed.

The third feature of the present invention relates to apoptosis-inducing food or beverage which contains an effective amount of fucoidan having an apoptosis-inducing ability derived from the fucoidan-containing substances.

The fourth feature of the present invention relates to apoptosis-inducing food or beverage which contains an effective amount of fucoidan having an apoptosis-inducing ability wherein algins derived from the fucoidan-containing substances are reduced or removed.

Incidentally, the term "algins" used in this specification stands for alginic acid and its salts and esters as well as degraded products thereof.

DESCRIPTION OF THE PREFERRED EMBODIMENTS

Figure 1:
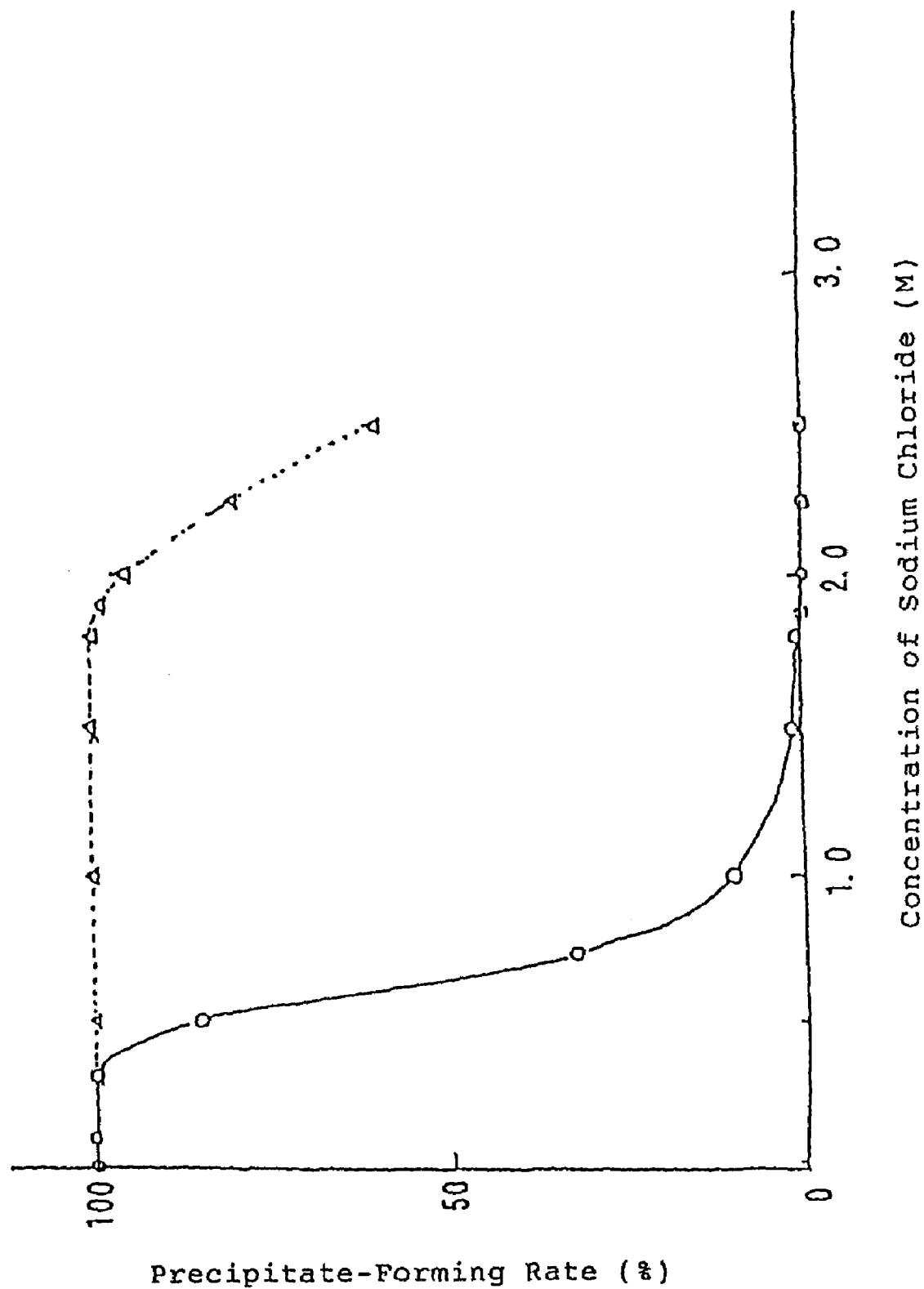
FIG. 1 shows the precipitate forming rates of fucoidan-U and fucoidan-F.

The present invention will be more specifically described below.

Fucoidan can be prepared from seaweed, trepang, etc. and, in the present invention, fucoidan prepared as such can be used. The use of seaweed and trepang containing high amount of fucoidan are particularly preferred in the present invention.

Examples of fucoidan of the present invention are fucoidan in a purified form and/or fucoidan-containing substances.

Examples of the fucoidan-containing substances are fucoidan-containing extracts.

The fucoidan-containing extracts include an extract from a raw material derived from fucoidan-containing substances and a product prepared by treating said extract where the extract containing a high amount of fucoidan is preferred.

Examples of said fucoidan-containing extract such as an extract of seaweed are extracts obtained by extracting the seaweed in the presence of calcium salt. Calcium chloride may, for example, be used as the calcium salt.

Examples of said seaweeds extract are soluble substances which are obtained by extracting the seaweed with an alkaline solution followed by adding a calcium salt to the extract. A sodium carbonate solution may, for example, be used as the alkaline solution while calcium chloride may, for example, be used as the calcium salt.

Examples of said seaweed extracts are the soluble substances which are obtained by extracting the seaweed with an alkaline solution followed by acidifying the resulting extract. A sodium carbonate solution may, for example, be used as the alkaline solution.

Temperature and time for extraction of raw materials derived from fucoidan-containing substances may be selected from the range of 40-200° C. and 1-360 minutes, respectively and, usually, they may be selected from the range of 50-130° C. and 10-180 minutes, respectively.

An example of the fucoidan which is used in the present invention is a substance where the fucoidan content is increased in an aqueous extract of the raw material derived from the fucoidan-containing substance and where the content of algins is substantially reduced or removed. In such a substance, it is possible to offer a material (1) having no properties such as high viscosity and acid coagulation caused by algins and gelation due to multivalent metal ions which have affected food and beverage, and (2) having no influence on the physical properties inherent to food and beverage.

Especially in the product prepared by treating the extract of seaweed with active carbon, only the smell of seaweed is selectively removed and said product is particularly preferred for use as food and beverage where the seaweed smell is not required.

Fucoidan used in the present invention can be supplied in large quantities starting from edible fucoidan-containing substance such as edible seaweed and trepang and it has an extremely high safety.

There is no particular limitation for the food and beverage of the present invention and the examples are processed cereals [such as processed wheat flour products, processed starch products, processed premix products, noodles, macaroni, bread, bean jams, soba (Japanese buckwheat noodles), fu (Japanese wheat gluten bread), biifun (Chinese bean jelly sticks), harusame (Japanese bean jelly sticks) and packed mochi (rice cake)], processed fat/oil products [such as plastic fat/oil, oil for deep frying, salad oil, mayonnaise and dressing], processed soybean products [such as tofu (soybean curd), miso (fermented soybean paste) and natto (fermented soybeans)], processed meat products [such as ham, bacon, press ham and sausage], marine products [such as frozen ground fish meat, kamaboko (boiled fish paste), chikuwa (another type of boiled fish paste), hanpen (fish cake), satsuma-age (fried fish balls), tsumire (boiled fish paste), suji (fish muscle products), fish meat ham, fish meat sausage, dried bonito, processed fish egg products, canned marine products and tsukudani (fish boiled down in soy sauce)], milk products [such as raw milk, cream, yogurt, butter, cheese, condensed milk, powdered milk and ice cream], processed vegetable/fruit products [such as pastes, jams, pickles, fruit beverages, vegetable beverages and mixed beverages], confectioneries [such as chocolate, biscuit, bun, cake, mochigashi (rice ball cake) and rice cracker], alcoholic beverages [such as Japanese sake wine, Chinese wine, wine, whisky, shochu (Japanese distilled spirits), vodka, brandy, gin, ram, beer, alcoholic beverage for refreshment, fruit wine and liquors], table beverages [such as green tea, tea, oolong tea, coffee, beverages for refreshment and lactic acid-beverages], condiments [such as soy sauce, Wooster sauce, vinegar and mirin (sweet sake)], canned, bottled or packed foods [gyumeshi (stewed beef with rice), kamameshi (boiled rice placed in a small kettle-like container), sekihan (rice boiled with red beans), curried rice and other retort foods)], semi-dried or concentrated foods [such as lever paste and other spread, soup for soba or udon and concentrated soup], dried foods [such as instant noodles, instant curry roux, instant coffee, powdery juice, powdery soup, instant miso soup and retort foods, beverages and soup], frozen food [such as frozen sukiyaki, chawan-mushi (pot-steamed hotch-potch), unagi-kabayaki (broiled eels), hamburger steak, shao-mai (Chinese steamed dumpling), gyoza (fried dumpling stuffed with minced pork, etc.), sticks and fruit cocktails], solid foods, liquid foods [such as soup], spikes and other processed agricultural, forest, stock raising and marine products.

There is no particular limitation for manufacturing the food and beverage of the present invention but any cooking and processing means and any of the manufacturing methods which have been usually conducted may be used provided that the resulting food or beverage contains fucoidan. When an effective amount of apoptosis-inducing fucoidan is added to food or beverage, it is possible to offer apoptosis-inducing food or beverage.

In the case of cooking and processing, fucoidan may be added before, during or after the cooking/processing. Alternatively, cooked or processed thing or a material therefor may be added to fucoidan so that fucoidan is diluted. In the manufacture of food or beverage, fucoidan may be added during any of the steps, or food or beverage or material thereof may be added to fucoidan so that fucoidan is diluted and is contained in the food or beverage. The addition may be conducted at one time or separately over several times. Thus, it is possible to easily manufacture the novel food or beverage or the apoptosis-inducing food or beverage having an apoptosis-inducing action containing an effective amount of fucoidan. In case any of the above-mentioned steps is applied, then the food or beverage where fucoidan is contained therein, added thereto and/or diluted therein and the apoptosis-inducing food or beverage where fucoidan is contained therein, added thereto and/or diluted therein containing an effective amount of fucoidan may be defined as the food or the beverage of the present invention.

The amount of fucoidan to be added to food was then investigated using a model beverage as described below.

INVESTIGATING EXAMPLE 1

In order to conduct a model test beverage, a 0.01M lactic acid buffer of pH 3.8 was prepared and then commercially available sucrose was dissolved therein to make the sucrose concentration 5 w/v % whereupon a sucrose solution was prepared. Fucoidan II of Example 1 was used and 0 (control), 0.1, 0.5, 1, 5, 10, 20, 30, 40, 50, 100, 150 and 200 mg w/v % of it were added whereupon the sucrose solutions containing fucoidan were prepared and were subjected to an organoleptic test for their feel upon drinking in terms of mellowness and smoothness on tongue, feel upon passing through the throat and a balance of the taste. Numbers of the panelists were 20 and the test was conducted by means of a five-point evaluation method (where 5 stands for good while 1 stands for bad). The results are given in Table 1 in terms of average values.

TABLE 1

Organoleptic Test of the Model Beverages

| Amount of Fucoidan Added | Touch on Tongue | | Feel passing the Throat | Balance of the Taste | Total Feel on Eating |
|---|---|---|---|---|---|
| (mg w/v %) | Mellowness | Smoothness | | | |
| 0 | 1.2 | 1.4 | 1.6 | 1.5 | 1.4 |
| 0.1 | 1.6 | 1.7 | 1.7 | 1.6 | 1.6 |
| 0.5 | 2.0 | 1.9 | 1.8 | 1.7 | 1.8 |
| 1 | 2.1 | 2.2 | 2.0 | 1.9 | 2.0 |
| 5 | 2.5 | 2.6 | 2.7 | 2.8 | 2.6 |
| 10 | 3.5 | 3.6 | 3.4 | 3.8 | 3.6 |
| 20 | 4.0 | 4.2 | 4.1 | 4.5 | 4.2 |
| 30 | 4.5 | 4.7 | 4.3 | 4.5 | 4.5 |
| 40 | 4.6 | 4.7 | 4.3 | 4.6 | 4.6 |
| 50 | 4.7 | 4.7 | 4.5 | 4.8 | 4.7 |
| 100 | 4.3 | 4.6 | 4.6 | 4.8 | 4.6 |
| 150 | 4.0 | 3.9 | 3.2 | 3.8 | 3.7 |
| 200 | 3.8 | 3.6 | 3.1 | 3.6 | 3.5 |

From Table 1, it is noted that, in view of feel on tongue, feel passing the throat and balance of the taste in the organoleptic evaluations, an effect is noted by addition of fucoidan, i.e. 0.1 mg w/v % or more concentrations.

INVESTIGATING EXAMPLE 2

To the model beverage of Example 1 containing 30 mg w/v % of fucoidan II was added alginic acid derived from seaweed in an amount of 0 (control), 5, 10, 20, 30, 40, 60, 80, 100, 150 or 200 mg w/v % and the influence of the ratio of fucoidan to alginic acid existing therein on the feel on eating was tested by means of the same organoleptic test as in Investigating Example 1. Average values of the results are given in Table 2.

TABLE 2

Influence of Fucoidan and Alginic Acid on Organoleptic Evaluations

| Alginic Acid | Fucoidan | Fucoidan Ratio* | Feel on Tongue | | Feel on the Throat | Balance of the Taste | Total Evaluation on Eating |
|---|---|---|---|---|---|---|---|
| (mg w/v %) | | | Mellowness | Smoothness | | | |
| 0 | 30 | 100 | 4.5 | 4.7 | 4.3 | 4.5 | 4.5 |
| 5 | 30 | 85 | 4.5 | 4.6 | 4.2 | 4.5 | 4.4 |
| 10 | 30 | 75 | 4.3 | 4.5 | 4.2 | 4.5 | 4.4 |
| 20 | 30 | 60 | 4.2 | 4.4 | 4.1 | 4.5 | 4.3 |
| 30 | 30 | 50 | 4.2 | 4.4 | 4.1 | 4.4 | 4.3 |
| 40 | 30 | 43 | 4.0 | 4.1 | 3.7 | 3.9 | 3.9 |
| 60 | 30 | 33 | 3.5 | 3.6 | 3.1 | 3.2 | 3.3 |
| 80 | 30 | 27 | 3.2 | 3.3 | 3.2 | 3.1 | 3.2 |
| 100 | 30 | 23 | 3.2 | 3.1 | 3.0 | 3.1 | 3.1 (remained a bit on tongue) |
| 150 | 30 | 17 | 2.9 | 2.8 | 2.5 | 3.0 | 2.8 (remained a bit on tongue) |
| 200 | 30 | 13 | 2.7 | 2.6 | 2.3 | 2.6 | 2.6 (remained a bit on tongue) |

*(Fucoidan)/(Alginic Acid + Fucoidan) (%)

It is noted from Table 2 that the effect on feel upon eating was highest in the model beverage when only fucoidan was added thereto and that, when the ratio of weight of fucoidan to that of alginic acid and fucoidan (hereinafter, referred to as a fucoidan ratio) becomes smaller, the evaluation of feel on eating becomes poor. In the organoleptic evaluation data, the effect achieved by addition of 10 mg w/v % of fucoidan was noted when the fucoidan ratio was 43% or more. The effect achieved by addition of 5 mg w/v % of fucoidan was noted when the fucoidan ratio was 13% or more while the cases where no remaining feel on tongue was noted were achieved when the ratio was 27% or more.

There is no particular limitation for the amount of fucoidan in food or beverage of the present invention but the amount may be appropriately selected by taking the organoleptic and physiological activities into consideration. For example, its amount calculated as fucose per 100 parts of food or beverage by a cysteine-sulfuric acid method is 0.001 part or more and, in view of the organolepticity as food or of the taste as beverage, in view of induction of apoptosis and also in view of the cost, said amount is preferably 0.005-10 parts or, more preferably, 0.01-1.0 part. Incidentally, the term "part(s)" used in this specification stands for that/those by weight.

There is no particular limitation for the form of the food or beverage of the present invention so far as fucoidan of the present invention is contained therein and said form includes that which can be orally taken such as tablets, granules, capsules, gel and sol.

The food or beverage of the present invention contains an effective amount of fucoidan having a physiological activity and, due to an apoptosis-inducing action or the like of said fucoidan, it is a healthy or functional food or beverage having an effect of preventing carcinogenesis or suppressing cancer. It is a food or beverage which is particularly useful in maintaining stomach and intestine in a healthy state.

In the present invention, fucoidan is a polysaccharide containing fucose sulfate in a molecule and/or a degraded product thereof and there is no particular limitation. Incidentally, the fucose-containing polysaccharide derived from brown algae plants is usually called fucoidan, fucoidin or fucan and, although several molecular species thereof have been known already, fucoidan of the present invention covers any and all of them.

Examples of a method for degradation of fucoidan are a chemically degrading method by treating it with an acid, etc., a physically degrading method by treating it with ultrasonic wave, etc., a method of degrading it with enzymes and a method of degrading it with microorganisms. In the present invention, any of the degraded fucoidans which contain sulfated fucose in the molecule and show an apoptosis-inducing action may be used.

In said fucoidan molecular species, there are a group where fucose is a main component and another group where several % of uronic acid is contained and, as constituting saccharides, much amounts of fucose and mannose are contained therein. Hereinafter, a group where uronic acid is not substantially contained therein will be referred to as fucoidan-F while another where uronic acid is contained therein will be referred to as fucoidan-U and a mixture of them will be just referred to as fucoidan.

In the present invention, one of fucoidan-F and fucoidan-U may be used solely or both of them may be used jointly. Thus, the food or beverage where pure fucoidan-F or fucoidan-U is a main component is covered by the present invention as well. Such a food or beverage containing an increased amount of said fucoidans, particularly fucoidan-U, has a potent effect for promoting the health.

The extract derived from fucoidan-containing natural products according to the present invention contains fucoidan-U having the following physical and chemical properties which is prepared, for example, by a method as shown in Example 4.

(1) component sugar: containing uronic acid; and (2) being degraded by the endo-fucoidan-lyase produced by *Flavobacterium* sp. SA-0082 (FERM BP-5402) to thereby form at least one of the compounds selected from those represented by the following formulae (I), (II) and (III).

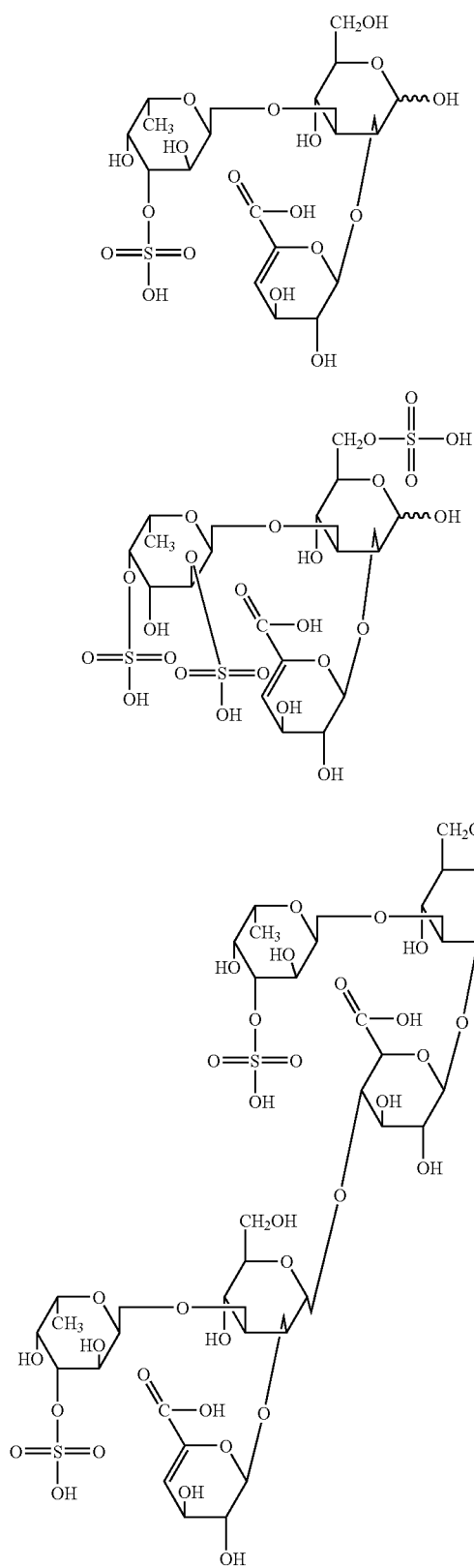

The extract derived from fucoidan-containing natural products according to the present invention contains fucoidan-F having the following physical and chemical properties which is prepared, for example, by a method as shown in Example 5.

(1) component sugar: substantially being free from uronic acid; and (2) substantially incapable of being degraded by the endo-fucoidan-lyase produced by *Flavobacterium* sp. SA-0082 (FERM BP-5402).

When fucoidan is treated with a fucoidan-degrading microorganism such as the above-mentioned endo-fucoidan-lyase productive *Flavobacterium* sp. SA-0082 (FERM BP-5402), a microbiologically degraded fucoidan can be prepared.

Further, when the above-mentioned fucoidan-U is treated with a endo-fucoidan-lyase such as that produced by *Flavobacterium* sp. SA-0082 (FERM BP-5402), enzymatically degraded fucoidan-U can be prepared. These degraded fucoidan and/or fucoidan-U can be easily fractionated according to their molecular weight. Food or beverage where those degraded fucoidans are contained therein, added thereto and/or diluted therewith is the food or beverage of the present invention as well.

In the manufacture of an extract derived from seaweed which is one of the examples of the fucoidan contained in the food or beverage of the present invention, the seaweed which is applicable is, for example, Rhodophyceae such as common laver (*Porphyra tenera*), *Gelidium cartilagimeum* and *Gracilaria confervoides*; Chlorophyceae such as *Ulva lactuca*; and Phaeophyceae such as *Ecklonia cava, Eisenia arboria* var. *bicyclis, Nemacystus dicipiens, Hizikia fusiforme, Undaria pinnatifida, Kjellmaniella crassifolia* and *Laminaria japonica* and, among them, seaweed containing high amount of fucoidan is particularly suitable in the present invention.

With respect to the seaweed used in the present invention, the seaweed which contains high amount of fucoidan such as Phaeophyceae may, for example, be directly dried, milled and extracted or the fresh one may be finely cut and extracted.

Any extracting method may be used so far as fucoidan can be efficiently extracted.

The process for the manufacture of a seaweed extract may contain a step of washing the seaweed with water, alcohol or aqueous alcohol. Extraction of seaweed may be conducted in the presence of alcohol as well.

In the present invention, seaweed is extracted, for example, with a solution of calcium salt such as calcium chloride to prepare an extract of seaweed with a calcium chloride solution.

It is preferred that the extraction is conducted using 10-1, 000 parts of calcium chloride solution to one part of dry seaweed and that the concentration of calcium chloride is 25 mM or more.

When fresh seaweed is used, it is preferred to use 1-100 parts of calcium chloride solution to one part of the fresh seaweed and that the concentration of calcium chloride is 25 mM or more.

It is preferred that the extraction is conducted within a range of 50-130° C. and 10-180 minutes. Any extracting condition may be adopted so far as the amount of algins in the extract is reduced whereby fucoidan can be efficiently extracted.

After completion of the extraction of the seaweed with a calcium salt solution, insoluble matters are removed. Method for the removal of the insoluble matters may be selected from centrifugation, filtration, etc. Calcium salt in the solution wherefrom the insoluble matters are removed can be removed, for example, by ultrafiltration or ion exchanging method. The solution wherefrom the calcium salt is removed can be further treated with active carbon, ion exchanger, etc. so that the seaweed smell can be selectively eliminated.

In the present invention, seaweed is, for example, extracted with an alkaline solution such as sodium carbonate solution to prepare an extract of the seaweed with sodium carbonate. Then calcium salt such as calcium chloride is added to said extract and the resulting insoluble matters are removed whereupon the soluble fractions of the seaweed-derived extract can be prepared.

It is preferred that the extraction is conducted using. 10-600 parts of sodium carbonate solution to one part of the seaweed and that the concentration of sodium carbonate is 0.1-5%.

When fresh seaweed is used, it is preferred that 1-60 parts of sodium carbonate solution is used to one part of the fresh seaweed and that the concentration of sodium carbonate is 0.1-5%.

It is preferred that the extraction is conducted within a range of 50-130° C. and 10-180 minutes. Any extracting condition may be adopted provided that fucoidan can be efficiently extracted in the extract. Incidentally, the term % used in this specification stands for that by weight.

After completion of extraction of the seaweed with a sodium carbonate solution, calcium salt such as calcium chloride is added thereto and the resulting insoluble components are removed. Amount of calcium chloride to be added is in such an extent that no more algins are precipitated by adding it to the sodium carbonate extract and any conditions will do so far as the algins in the extract can be efficiently precipitated. Method for the removal of the resulting insoluble components may be selected from centrifugation, filtration, etc. The salts such as sodium carbonate and calcium chloride in the solution wherefrom the insoluble components are removed can be removed by, for example, means of ultrafiltration and ion exchanging. The solution wherefrom the salts are removed may be further treated with active carbon, ion exchanger, etc. so that its seaweed smell can be selectively eliminated.

In the present invention, the seaweed is, for example, extracted with an alkaline solution such as sodium carbonate solution to prepare an extract of seaweed with sodium carbonate. After that, the extract is acidified with an acid such as diluted sulfuric acid and the resulting insoluble components are removed whereupon a soluble substance of the seaweed-derived extract is prepared.

Extraction of the seaweed with a sodium carbonate solution is conducted according to a method which was mentioned already.

After completion of extraction of the seaweed with a sodium carbonate solution, an acid solution such as diluted sulfuric acid is added thereto and the resulting insoluble components are removed. Amount of the diluted sulfuric acid to be added is in such an extent that pH of the extract with sodium carbonate becomes 1-2.5 and any conditions will do so far as the extract is made acidic whereby the algins in the extract can be efficiently precipitated. Method for the removal of the resulting insoluble components may be selected from centrifugation, filtration, etc. The salts in the solution wherefrom the insoluble components are removed can be eliminated by, for example, means of ultrafiltration and ion exchanging. The solution wherefrom the salts are removed may, if necessary, be neutralized and, when the acidic or neutralized solution may be further treated with active carbon, ion exchanger, etc. so that its seaweed smell can be selectively eliminated.

Fucoidan of the present invention may be either liquid or solid. In the manufacture of solid fucoidan, known methods such as a spray-drying method and a freeze-drying method may be suitably selected.

Usually, fucoidan is weak to acids and alkalis and, therefore, it is apt to be degraded into low molecular substances when an acidic or alkaline solution is used. When heating temperature, heating time, pH, etc. are appropriately adjusted, it is possible to prepare a desired degraded product. It is possible to adjust the average molecular weight and the molecular weight distribution by, for example, means of gel filtration, treatment with membrane for fractionating the molecular weight, etc. Molecular weight and sugar component of fucoidan vary depending upon the harvest time of the material for fucoidan, the method for drying said material, the method for storing said material, etc. and also depending upon heating conditions, pH conditions, etc. during the extracting process of fucoidan. For example, fucoidan is hydrolyzed by acid while, under an alkaline condition, it becomes to low molecular products as a result of a β-elimination of uronic acid. Accordingly, with respect to fucoidan-U and fucoidan-F mentioned in this specification, the molecular weight and the molecular weight distribution given therefor are just examples and can be easily changed by adjusting the treating conditions for fucoidan. For example, when fucoidan is heated at 100° C. for one hour under a weakly alkaline condition and when a molecular sieve membrane having a pore size of 300 is used for removal of the salt, it is possible to prepare fucoidan, fucoidan-U, fucoidan-F, etc. having a molecular weight distribution of from about 1,000 to about 10,000. Depending upon the conditions applied, fucoidan having any molecular weight and any molecular weight distribution can be prepared and such a product may be used as a fucoidan of the present invention.

When fucoidan and/or degraded product thereof in accordance with the present invention are/is added to a culture liquid of cancer cells, apoptosis is resulted in said cancer cells after one to several days from the addition. Incidentally, they do not show toxicity to normal cells. Particularly, fucoidan derived from edible seaweed and/or degraded product thereof have/has a high safety.

The present invention will be further illustrated by way of the following examples although the present invention is never limited by those examples.

EXAMPLE 1

(1) *Kjellmaniella crassifolia* was well dried and 20 kg of the dried one was milled by a free disintegrator (mfd. by Nara Kikai Seisakusho).

Calcium chloride dihydrate (7.3 kg) (mfd. by Nippon Soda) was dissolved in 900 liters of tap water and mixed with 20 kg of the milled *Kjellmaniella crassifolia*. Steam was blown thereinto whereby the liquid temperature was raised from 12° C. to 90° C. within 40 minutes, then the temperature was kept at 90-95° C. for one hour with stirring and cooled to give 1,100 liters of cooled mixture.

This was subjected to a treatment with a solid-liquid separator (type CNA; mfd. by Westfalier Separator) to separate the cooled mixture into solid and liquid whereupon about 900 liters of a supernatant liquid was prepared.

The supernatant liquid (360 liters) was concentrated to 20 liters using an FE10-FC-FUS0382 (cut off molecular weight: 30, 000) (mfd. by Daicel). To this was added 20 liters of tap water followed by concentrating to 20 liters and such operations were repeated for five times to remove the salt therefrom whereupon 25 liters of an extract solution derived from seaweed containing high amount of fucoidan was prepared.

The extract solution had a pH of about 6.5, acidity of 0.06 ml, sugar degree of 0.8 Brix % and calcium concentration of 1,200 ppm.

Said solution (one liter) was freeze-dried to give 13 g of a dried product in which 65% of fucoidan and 33% of fucoidan-U were contained.

Content of fucoidan-U was measured by means of an HPLC using a standard fucoidan-U substance which was prepared in Example 4.

Incidentally, content of fucoidan was calculated by the following sulfuric acid-cysteine method using an aqueous solution of the standard fucoidan (0.4 mg/ml) prepared in Example 5.

The testing solution (200 µl) was taken in a test tube, 900 µl of a 6:1 mixture of concentrated sulfuric acid and water was added thereto under cooling with ice and the resulting mixture was well cooled and stirred. This was kept at about 20° C. for three minutes and heated in a boiling water bath for ten minutes. After heating, it was cooled in ice water and 20 µl of a 3% cysteine-hydrochloric acid was added followed by stirring (a colored section). As a control, 20 µl of water were added thereto followed by stirring (a blank). After stirring, the mixture was allowed to stand for one hour and the absorbances at 400 nm and 460 nm were measured.

Amount of fucoidan in the tested solution was calculated by the following formula.

Amount (mg/ml)=Test Solution [Colored Section $(A_{400}-A_{460})$-Blank $(A_{400}-A_{460})$]/Standard Solution [Colored Section $(A_{400}-A_{460})$-Blank $(A_{400}-A_{460})$]×diluting ratio×20.4

In the formula, $A_{400}$ is an absorbance at 400 nm while $A_{460}$ is that at 460 nm.

Incidentally, pH was measured by a pH meter while acidity was expressed by the amount (ml) of 0.1N NaOH required for neutralizing 10 ml of the sample solution to pH 7.0. Sugar degree was measured by a Brix saccharometer while concentration of calcium was measured by means of atomic absorption spectrometry.

Then, to the extract solution derived from seaweed containing high amount of fucoidan was added 2% of active carbon (available as a food additive; Shirasagi Brand) and the mixture was treated for 30 minutes, roughly filtered and finally filtered using a 0.8 µm filter to prepare a filtrate (fucoidan I) passing through a filter. Then one half of the filtrate was heated at 120° C. for 60 minutes with pressure to prepare a thermally treated liquid (fucoidan II).

The filtrate passed through the filter was freeze-dried and 10 mg of the dried product was suspended in each 10 ml of 1% sodium carbonate solution and 100 mM calcium chloride solution. In both solutions, the dried product was completely dissolved and no contamination with algins was noted.

(2) *Kjellmaniella crassifolia* was well dried and 20 kg of the dried product was milled using a disintegrator (Fitz Mill; mfd. by Hosokawa Micron).

Calcium chloride dihydrate (mfd. by Nippon Soda) (7.2 kg) was dissolved in 400 liters of tap water followed by mixing with 20 kg of milled *Kjellmaniella crassifolia*. Steam was blown into the mixture with stirring for 95 minutes whereby the liquid temperature was raised from 28° C. to 95° C. and the mixture was kept at 95° C. for two hours with stirring and cooled to give 500 liters of cooled product.

The cooled product was subjected to a solid-liquid separation using a solid-liquid separator (mfd. by Tanabe Weltech) to prepare about 450 liters of a supernatant liquid after the solid-liquid separation.

Said supernatant liquid was concentrated to 40 liters using an FE10-FC-FUS0382 (cut off molecular weight: 30,000) (mfd. by Daicel). After that, sterilized water by filtration was continuously added thereto to make the flow rate 40-60 liters/hour and a desalting treatment was conducted therefor until electroconductivity became 1.0 mS/cm$^2$ whereupon 40 liters of an extract solution derived from seaweed containing high amount of fucoidan was prepared.

Then, to said extract solution were added 0.4 kg of Celite #545 (mfd. by Celite) and 0.4 kg of Silica #600-S (mfd. by Chuo Silica) as the filtering aids and the mixture was filtered using a compact filter (16 stage×6 inches; filter paper: ADVANTEC #327) precoated with 0.1 kg of Celite # 545 and 0.1 kg of Silica #600-S.

The resulting filtrate was subjected to a continuous instant heating treatment using a plate heater (mfd. by Nichihan Seisakusho) at 98° C. for 60 seconds and cooled to prepare 46 liters of an extract solution (fucoidan V) derived from seaweed containing high amount of fucoidan.

Said extract solution had a pH of about 7, acidity of 0 ml, sugar degree of 1.2 Brix %, calcium concentration of 920 ppm, solid content of 1.2% and fucoidan content of 17 mg/ml. Neither alginic acid nor iodine was detected.

The content of alginic acid was measured by means of an HPLC using a commercially available alginic acid as a standard substance.

The content of fucoidan was calculated by means of a sulfuric acid-cysteine method using an aqueous solution (0.4 mg/ml) of a standard fucoidan substance prepared in Example 5 as a standard solution.

Electroconductivity was measured by an electroconductivity meter. Iodine was separated by bromine and was titrated with sodium thiosulfate. Solid content was determined from the dry weight after a treatment with centrifugal evaporator (at 60° C. for 18 hours).

(3) *Kjellmaniella crassifolia* was well dried and 20 kg of the dried product was milled using a disintegrator (Fitz Mill; mfd. by Hosokawa Micron).

Calcium chloride dihydrate (mfd. by Nippon Soda) (7.3 kg) was dissolved in 400 liters of tap water followed by mixing with 20 kg of milled *Kjellmaniella crassifolia*. Steam was blown into the mixture with stirring for 95 minutes whereby the liquid temperature was raised from 28° C. to 95° C. and the mixture was kept at 95° C. for two hours with stirring and cooled to give 500 liters of cooled product.

The cooled product was subjected to a solid-liquid separation using a solid-liquid separator (mfd. by Tanabe Weltech) to prepare about 450 liters of supernatant liquid after the solid-liquid separation.

Said supernatant liquid was concentrated to 40 liters using an FE10-FC-FUS0382 (cut off molecular weight: 30,000) (mfd. by Daicel). After that, sterilized water by filtration was continuously added thereto to make the flow rate 30 liters/hour and a desalting treatment was conducted therefor until electroconductivity became 1.0 mS/cm$^2$ whereupon 34 liters of an extract solution derived from seaweed containing high amount of fucoidan were prepared.

After that, 1.1 kg of pectin (Pomocin Pectin LM-13CG; mfd. by Hercules) was added to 20 liters of tap water, steam was blown thereinto so that the liquid temperature was raised from 28° C. to 120° C. for 35 minutes and the mixture was kept at 120° C. for five hours with stirring and cooled to prepare 28 liters of a cooled product.

Then 34 liters of the extract solution derived from seaweed containing high amount of fucoidan were mixed with 28 liters of heat-treated pectin and the mixture was adjusted to pH 3.5 with citric anhydride (mfd. by Fuso Kagaku). After that, 0.9 kg of Celite #545 (mfd. by Celite) and 0.8 kg of Silica #600-S (mfd. by Chuo Silica) were added as filtering aids thereto and the mixture was filtered using a compact filter (16 stage×6 inches; filter paper: ADVANTEC #327) precoated with 0.2 kg of Celite #545 and 0.2 kg of Silica #600-S.

To the resulting filtrate was added 18 liters of pure water and the resulting mixture was subjected to a continuous instant heating treatment using a plate heater (mfd. by Nichihan Seisakusho) at 98° C. for 60 seconds and cooled to prepare 80 liters of an extract solution (fucoidan VI) derived from seaweed containing high amount of fucoidan.

Said extract solution had a pH of about 3.5, acidity of 1.7 ml, sugar degree of 2.1 Brix %, calcium concentration of 710 ppm, solid content of 2.0%, fucoidan content of 13 mg/ml and fucoidan-U content of 6.6 mg/ml. Neither alginic acid nor iodine was detected.

One liter of said solution was freeze-dried to give 20 g of a dried product.

EXAMPLE 2

Fresh *Laminaria japonica* was finely cut, 200 g of the resulting finely cut one were suspended in 600 ml of a 1% aqueous solution of sodium carbonate, the suspension was heated at 60° C. for one hour and water was added thereto to make the whole volume one liter. This solution was centrifuged, the supernatant liquid was collected and water was added thereto to make the whole volume four liters.

To this solution was added 500 mM of calcium chloride until no more precipitate was formed and the resulting precipitate was removed by a filter paper. The resulting filtrate was concentrated and desalted with a Microacilyzer to prepare 3.6 liters of a desalted solution. One half of it was freeze-dried to give 2.1 g of an extract fraction (fucoidan III) derived from seaweed containing high amount of fucoidan. Another half of the desalted solution was treated with 2% active carbon followed by heating with pressure at 120° C. for 60 minutes to prepare a heat-treated solution (fucoidan IV).

The above freeze-dried product (10 mg) was suspended in each 10 ml of a 1% sodium carbonate solution and a 100 mM calcium chloride solution. In both solutions, said fraction was completely dissolved and no contamination of algins was noted.

EXAMPLE 3

Apoptosis-Inducing Activity of the Extracts Derived from Seaweed Containing High Amount of Fucoidan Prepared in Examples 1 and 2

Human promyelocytic leukemia cells HL-60 (ATCC CCL-240) which was incubated at 37° C. in an RPMI 1640 medium (mfd. by Gibco) containing 10% of fetal calf serum (JRH Bioscience) treated at 56° C. for 30 minutes was suspended in an ASF 104 medium (mfd. by Ajinomoto) to make a suspension containing $5 \times 10^5$ cells/9 ml. To 9.0 ml of this suspension was added 1 ml of each of the solutions of extract (fucoidan I and III) derived from seaweed containing high amount of fucoidan prepared in Examples 1 and 2 [prepared by dissolving each of the fucoidans in 50 mM HEPES buffer (pH 7.2) containing 100 mM of sodium chloride to make 5 mg/ml concentration followed by sterilizing at 121° C. for 20 minutes] and each mixture was incubated at 37° C. for 18 hours in the presence of 5% carbon dioxide. The incubated cells were centrifuged to separate from a supernatant liquid. The resulting cells were suspended in 20 μl of a 50 mM Tris hydrochloride buffer (pH: 7.8) containing 10 mM of ethylenediamine tetraacetate and 0.5% of sodium lauroyl sarcosinate, then 1 μl of ribonuclease A (10 mg/ml) (mfd. by Sigma) was added thereto followed by treating at 50° C. for 30 minutes and 1 μl of proteinase K (10 mg/ml) was added thereto followed by treating at 50° C. for one hour. The cells after the treatment were used as a sample and subjected to an electrophoresis using a 2% agarose gel under constant voltage of 100 volts. The gel was dipped in ethidium bromide for 30 minutes and then the state of DNA in the gel was checked using a transilluminator whereupon a DNA ladder which was specific to apoptosis was confirmed.

It was now apparent from this result that apoptosis was induced in HL-60 cells by the extracts derived from seaweed containing high concentration of fucoidan prepared in Examples 1 and 2.

Further, each of said extracts (fucoidan II and fucoidan IV) derived from seaweed containing high amount of fucoidan prepared in Examples 1 and 2 was dissolved in a physiological saline solution to make a 5 mg/ml solution followed by sterilizing at 121° C. for 20 minutes and the resulting solution was used as a test solution for measuring the apoptosis-inducing activity according to the above-mentioned method whereupon the same effect was confirmed for each of the test solutions.

After that, human promyelocytic leukemia cells HL-60 which was incubated at 37° C. in an RPMI 1640 medium (mfd. by Gibco) containing 10% of fetal calf serum (JRH Bioscience) treated at 56° C. for 30 minutes was suspended in an ASF 104 medium (mfd. by Ajinomoto) to make a suspension containing $2.5 \times 10^5$ cells/4.5 ml. To 4.5 ml of this suspension was added 0.5 ml of each of the solutions of extract (fucoidan I and III) derived from seaweed containing high amount of fucoidan prepared in Examples 1 and 2 [prepared by dissolving each of the fucoidans in 50 mM HEPES buffer (pH 7.2) containing 100 mM of sodium chloride to make 2 mg/ml, 5 mg/ml and 10 mg/ml concentrations followed by sterilizing at 121° C. for 20 minutes] and each of the mixtures was incubated at 37° C. in the presence of 5% carbon dioxide. After 24 hours and 44 hours from the initiation of the incubation, each 0.5 ml of the culture liquid was taken out as a sample and the viable cell numbers in the medium were counted by a method mentioned in "Techniques in Tissue Culture" (second edition) (published by Asakura Shuppan; edited by Japan Tissue Culture Society; published on Nov. 1, 1990; pages 26-28). Thus, the counting was conducted by a method where the cells were dyed with Trypan Blue on a hemocytometer.

Figure 2:
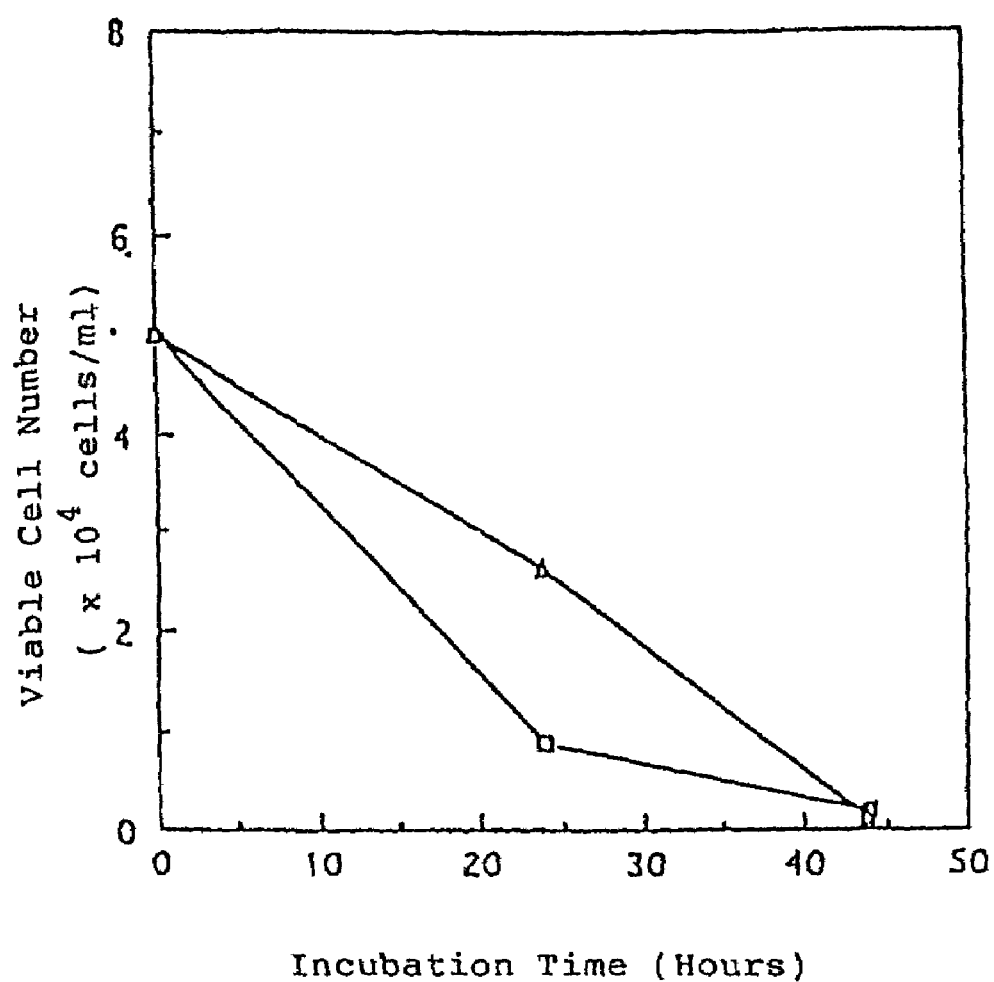
FIG. 2 shows an apoptosis-inducing action of an extract (0.2 mg/ml) derived from seaweed.
Figure 3:
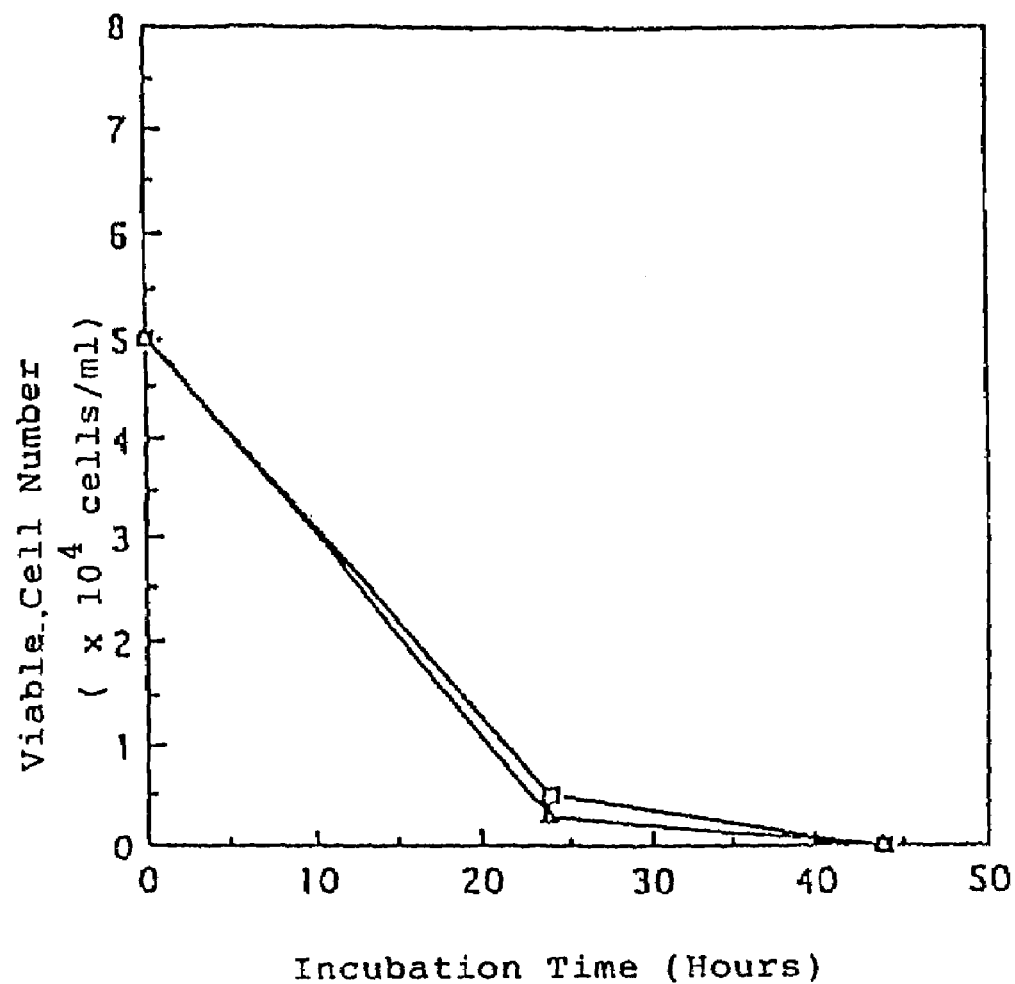
FIG. 3 shows an apoptosis-inducing action of an extract (0.5 mg/ml) derived from seaweed.
Figure 4:
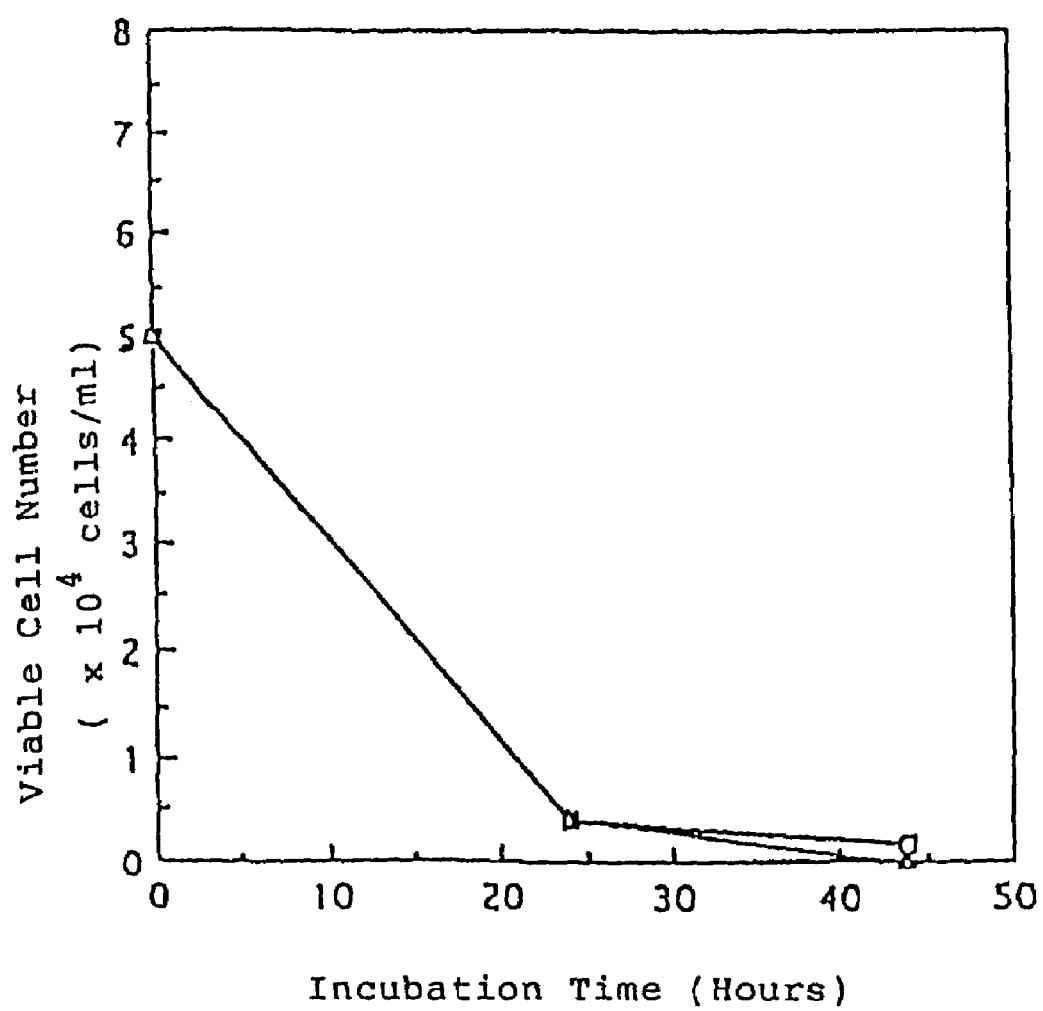
FIG. 4 shows an apoptosis-inducing action of an extract (1 mg/ml) derived from seaweed.

The results are shown in FIGS. 2-4. FIG. 2 shows proliferation of the cells in the presence of 0.2 mg/ml of each fucoidan where the ordinate shows the viable cell numbers per ml of the culture liquid ($\times 10^4$/ml; this will be applied to the descriptions hereinafter as well) while the abscissa shows incubation time (hours). FIG. 3 shows proliferation of the cells in the presence of 0.5 mg/ml of each fucoidan where the ordinate shows the viable cell numbers per ml of the culture liquid while the abscissa shows incubation time (hours). FIG. 4 shows proliferation of the cells in the presence of 1 mg/ml of each fucoidan where the ordinate shows the viable cell numbers per ml of the culture liquid while the abscissa shows incubation time (hours). In each of FIGS. 2-4, an open triangle stands for the viable cell numbers at each of the incubation time in the presence of an extract (fucoidan I) derived from seaweed containing high amount of fucoidan prepared in Example 1 while an open square stands for the viable cell numbers at each of the incubation time in the presence of an extract (fucoidan III) derived from seaweed containing high amount of fucoidan prepared in Example 2. Incidentally, in the control where no sample was added, the viable cell numbers in the culture liquid were $1.5 \times 10^5$/ml and $3.1 \times 10^5$/ml after incubations for 24 and 44 hours, respectively.

As shown in FIG. 2-4, the extract derived from seaweed containing high amount of fucoidan was capable of killing the HL-60 cells by means of apoptosis within two days provided that its concentration in the medium was at least 200 µg/ml.

Further, each of said extracts (fucoidan II, fucoidan IV, fucoidan V and fucoidan VI) derived from seaweed containing high amount of fucoidan prepared in Examples 1 and 2 was dissolved in a physiological saline solution to make 2-10 mg/ml solutions followed by sterilizing at 121° C. for 20 minutes. The resulting solutions were used as test solutions for measuring the apoptosis-inducing activity according to the above-mentioned method whereupon the same effect was confirmed for each of the test solutions.

EXAMPLE 4

Preparation of Fucoidan-U

*Kjellmaniella crassifolia* was well dried, 2 kg of the dried one was milled by a free disintegrator (mfd. by Nara Kikai Seisakusho), the resulting dried powder was suspended in nine liters of 80% ethanol and the suspension was heated at 80° C. for two hours. After that, this was filtered through a filter paper to give a residue. The residue was subjected to the above mentioned operations of washing with ethanol and filtration thereafter and said operations were repeated for three times whereupon an ethanol-washed residue was obtained. This was suspended in 36 liters of 0.2M calcium acetate solution, heated at 95° C. for two hours and filtered. The residue was washed with four liters of a 0.2M calcium acetate solution to give 36 liters of a fucoidan extract of *Kjellmaniella crassifolia*.

The above filtrate was concentrated to two liters by an ultrafiltrater equipped with an ultrafiltration membrane having an exclusion molecular weight of 100,000, salt was added thereto to make its final concentration 1.5M and then 5% cetyl pyridinium chloride was added thereto until no more precipitate was formed. The precipitate obtained thereby was removed by centrifugation. The resulting supernatant liquid was concentrated to one liter by means of ultrafiltration, four liters of ethanol was added thereto and the resulting precipitate was collected by means of centrifugation. To this precipitate was added 100 ml of a 4M aqueous sodium chloride solution, the mixture was well stirred, ethanol was added to make its concentration 80% and the mixture was stirred and centrifuged to give a precipitate. The precipitate was suspended in 80% ethanol followed by subjecting to centrifugation and such operations were repeated until the absorption in the supernatant liquid at 260 nm disappeared. The resulting precipitate was dissolved in two liters of a 2M aqueous solution of sodium chloride, the resulting insoluble matters were removed by means of centrifugation, 50 ml of DEAE-Cellofine A-800 (mfd. by Seikagaku Kogyo) was added thereto, the mixture was stirred and the resin added was removed by filtration. The filtrate was treated with a column of DEAE-Cellofine A-800 equilibrated with a 2M aqueous solution of sodium chloride, the nonadsorbed matters were subjected to ultrafiltration by an ultrafiltratet equipped with a holofiber which was able to exclude the molecular weight of 100,000 and less whereupon coloring substances and salt were completely removed and then the insoluble matters were removed by means of centrifugation and filtration followed by freeze-drying to prepare fucoidan-U. Weight of the freeze-dried fucoidan-U was 15 g.

FIG. 1 shows the precipitate forming ability of this fucoidan-U and fucoidan-F which was prepared in the following Example 5 in various concentrations of sodium chloride in the presence of an excessive amount of cetyl pyridinium chloride.

In FIG. 1, the ordinate refers to the precipitation ratio (%) while the abscissa refers to the concentration (M) of sodium chloride. The solid line with open circles stands for the precipitation ratio of fucoidan-U of the present invention at various sodium chloride concentrations (M) while the dotted line with open triangles stands for the precipitation ratio of the fucoidan-F of the present invention at various sodium chloride concentrations (M).

The precipitation ratios are determined at a solution temperature of 37° C. in the following manner.

Fucoidan-U and fucoidan-F are each dissolved in water and in a 4 M of sodium chloride solution at a concentration of 2% each. Then these solutions are mixed at various ratios to thereby give 125 µl portions of fucoidan-U and fucoidan-F solutions having various sodium chloride concentrations. Next, cetylpyridinium chloride is dissolved in water and 4 M of sodium chloride at a concentration of 2.5% and the obtained solutions are mixed at various ratios to thereby give 1.25% solutions of cetylpyridinium chloride with various sodium chloride concentrations.

3.2 times by volume as much the 1.25% solution of cetylpyridinium chloride is needed to completely precipitate fucoidan-U and fucoidan-F each dissolved in water at a concentration of 2%. To 125 µl portions of 2% solutions of fucoidan-U and fucoidan-F with various sodium chloride concentrations are added 400 µl portions of cetylpyridinium chloride solutions with various sodium chloride concentrations. After thoroughly stirring and allowing to stand for 30 minutes, each mixture is centrifuged and the sugar content of the supernatant is determined by the phenol-sulfuric acid method [Analytical Chemistry, 28, 350 (1956)] followed by the calculation of the precipitation ratio of each fucoidan at each sodium chloride concentration.

The molecular weight of fucoidan-U thus obtained is determined by the gel filtration method with the use of Sephacryl S-500. As a result, it shows a molecular weight distribution around about 190,000.

Next, the components of fucoidan-U are analyzed.

First, the fucose content is determined in accordance with the method described in Journal of Biological Chemistry, 175, 595 (1948).

Next, the dry preparation of fucoidan-U thus obtained is dissolved in 1 N hydrochloric acid to give a concentration of 0.5% and treated at 110° C. for two hours to thereby hydrolyze into constituting sugars. Subsequently, the reducing ends of the monosaccharides obtained by the hydrolysis are pyridyl-(2)-aminated (PA) by using GlycoTAG and Glyco-TAG Reagent Kits (each mfd. by Takara Shuzo) and the composition ratio of the constituting sugars is analyzed by an HPLC.

Next, the content of uronic acid is determined in accordance with the method described in Analytical Biochemistry, 4, 330 (1962).

Subsequently, the content of sulfuric acid is determined in accordance with the method described in Biochemical Journal, 84, 106 (1962).

As a result, it is found out that the constituting sugars of fucoidan-U are fucose, mannose, galactose, glucose, rhamnose, xylose and uronic acid and no other neutral sugar is substantially contained therein. The composition ratio by mol of the major components is as follows; fucose:mannose:galactose:uronic acid:sulfate group=about 10:7:4:5:20.

Structure of fucoidan-U was determined as follows.

Degradation of fucoidan-U with degrading enzyme capable of degrading fucoidan-U and purification of the degradation product:

The purified fucoidan-U is treated with an endo-fucoidan-lyase as will be described hereinafter and the degradation products are purified.

Namely, 16 ml of a 1% solution of fucoidan-U, 12 ml of a 50 mM phosphate buffer (pH 8.0), 4 ml of a 4M solution of sodium chloride and 8 ml of a 32 mU/ml solution of the endo-fucoidan-lyase are mixed together and made to react at 25° C. for 48 hours. It is confirmed that the absorbance of the reaction mixture at 230 nm is elevated as the reaction proceeds, thus proving that the degradation of fucoidan-U with this enzyme is in progress. After desalting with a Micro Acilyzer G3 (mfd. by Asahi Chemical Industry), the reaction mixture is separated into three fractions (a), (b) and (c) with a DEAE-Sepharose FF.

The above-mentioned endo-fucoidan-lyase is prepared in the following manner.

This strain was isolated by the present inventors from seawater in Aomori. It is indicated as *Flavobacterium* sp. SA-0082 and has been deposited at National Institute of Bioscience and Human-Technology, Agency of Industrial Science and Technology (1-3, Higashi 1-chome, Tsukuba, Ibaragi, 305 Japan) under the accession number FERM P-14872 since Mar. 29, 1995 and deposited at National Institute of Bioscience and Human-Technology as described above under the accession number FERM BP-5402 (transfer to international deposition being requested on Feb. 15, 1996).

This strain was isolated by the present inventors from the seawater in Aomori. It is indicated as *Flavobacterium* sp. SA-0082 and has been deposited at National Institute of Bioscience and Human-Technology, Agency of Industrial Science and Technology (1-3, Higashi 1-chome, Tsukuba, Ibaragi, 305 Japan) under the accession number FERM P-14872 since Mar. 29, 1995 and deposited at National Institute of Bioscience and Human-Technology as described above under the accession number FERM BP-5402 (transfer to international deposition being requested on Feb. 15, 1996).

The nutrients to be added to the medium for cultivating this strain may be arbitrary ones so long as the strain employed can utilize them so as to produce the endo-fucoidan-lyase. Appropriate examples of the carbon source include fucoidan, marine algae powder, alginic acid, fucose, glucose, mannitol, glycerol, saccharose, maltose, lactose and starch while appropriate examples of the nitrogen source include yeast extract, peptone, casamino acids, corn steep liquor, meat extract, defatted soybean, ammonium sulfate and ammonium chloride. The medium may further contain inorganic matters and metal salts such as sodium salts, phosphates, potassium salts, magnesium salts and zinc salts.

The yield of the endo-fucoidan-lyase produced by cultivating the strain varies depending on the cultivation conditions. In general, it is preferable that the cultivation temperature ranges from 15 to 30° C. and the pH value of the medium ranges from 5 to 9. The yield of the endo-fucoidan-lyase attains the maximum by cultivating the strain under aeration and agitation for 5 to 72 hours. As a matter of course, the cultivation conditions are appropriately selected depending on the strain employed, the medium composition, etc. so as to achieve the maximum yield.

The endo-fucoidan-lyase is contained in both of the cells and the culture supernatant.

The above-mentioned *Flavobacterium* sp. SA-0082 is cultivated in an appropriate medium and the cells are harvested and disrupted by means commonly employed for disrupting cells such as ultrasonication. Thus a cell-free extract can be obtained.

Subsequently, the extract is purified by a purification procedure commonly employed in the art to thereby give a purified enzyme preparation. For example, the purification may be effected by salting out, ion exchange chromatography, hydrophobic bond column chromatography, gel filtration or the like to thereby give the purified endo-fucoidan-lyase free from any other endo-fucoidan-lyase.

The culture supernatant obtained by eliminating the cells from the above-mentioned culture medium also contains a large amount of this enzyme (extracellular enzyme) which can be purified by the same means as those employed for purifying the intracellular enzyme.

Now an example of the purification of the endo-fucoidan-lyase will be given.

*Flavobacterium* sp. SA-0082 (FERM BP-5402) is inoculated into 600 ml of a medium comprising an artificial seawater (pH 7.5, mfd. by Jamarin Laboratory) containing 0.25% of glucose, 1.0% of peptone and 0.05% of yeast extract which has been pipetted into a two-liter Erlenmeyer flask and sterilized at 120° C. for 20 minutes. Then the strain is cultivated therein at 24° C. for 24 hours to thereby give a seed culture. Into a thirty-liter jar fermenter is fed 20 liters of a medium comprising an artificial seawater (pH 7.5, mfd. by Jamarin Laboratory) containing 0.25% of glucose, 1.0% of peptone, 0.05% of yeast extract and 0.01% of a defoaming agent (KM70 mfd. by Shin-Etsu Chemical Co., Ltd.) and sterilized at 120° C. for 20 minutes. After cooling, the medium is inoculated with 600 ml of the above-mentioned seed culture, which is then cultivated therein at 24° C. for 24 hours under aerating at a rate of 10 liters/min and agitating at 125 rpm. After the completion of the cultivation, the culture medium is centrifuged to thereby collect the cells.

These cells are suspended in a 20 mM acetate phosphate buffer (pH 7.5) containing 200 mM of sodium chloride, disrupted by ultrasonication and centrifuged to thereby give a cell extract. The endo-fucoidan-lyase in this cell extract shows an activity of 5 mU/ml of the medium.

To this extract is added ammonium sulfate so as to establish 90% saturation finally. After dissolving by stirring, the mixture is centrifuged and the precipitate is suspended in the same buffer as the above-mentioned one in which the cells are suspended. Then the suspension is thoroughly dialyzed against a 20 mM acetate phosphate buffer (pH 7.5) containing 50 mM of sodium chloride. After eliminating the precipitate formed by the dialysis by centrifugation, it is absorbed by a DEAE-Sepharose FF column which has been equilibrated with a 20 mM acetate-phosphate buffer (pH 7.5) containing 50 m of sodium chloride. Then the adsorbed matter is well washed with the same buffer and developed by a linear gradient elution with sodium chloride of 50 mM to 600 mM. The active fractions are combined and sodium chloride is added thereto so as to give a final concentration of 4 M. Next, it is adsorbed by Phenyl Sepharose CL-4B column which has been equilibrated with a 20 mM phosphate buffer (pH 8.0) containing 4 M of sodium chloride. Then the adsorbed matter is well washed with the same buffer and developed by a linear gradient elution with sodium chloride of 4 M to 1 M. The active fractions are combined and concentrated with an ultra-filtrater. Next, it is subjected to gel filtration with the use of Sephacryl S-300 which has been equilibrated with a 10 mM phosphate buffer containing 50 mM of sodium chloride. The active fractions are combined. The molecular weight of the enzyme determined from the retention time in Sephacryl S-300 is about 460,000. Next, the active fraction is dialyzed against a 10 mM phosphate buffer (pH 7) containing 250 mM of sodium chloride. The enzyme solution is adsorbed by a Mono Q HR5/5 column which has been equilibrated with a 10 mM phosphate buffer (pH 7) containing 250 mM of sodium chloride. The adsorbed matter is well washed with the same buffer and developed by a linear gradient elution with sodium chloride of 250 mM to 450 mM. The active fractions are combined to thereby give the purified enzyme. Table 3 summarizes the above-mentioned purification steps.

TABLE 3

| Step | Total protein (mg) | Total activity (mU) | Specific activity (mU/mg) | Yield (%) |
|---|---|---|---|---|
| Cell extract | 61,900 | 101,000 | 1.63 | 100 |
| Ammonium sulfate-precipitation | 33,800 | 88,600 | 2.62 | 87.7 |
| DEAE-Sepharose FF | 2,190 | 40,400 | 18.4 | 40.0 |
| Phenyl Sepharose CL-4B | 48.2 | 29,000 | 601 | 28.7 |
| Sephacryl S-300 | 7.24 | 19,600 | 2,710 | 19.4 |
| Mono Q | 0.824 | 15,000 | 18,200 | 14.9 |

The activity of this enzyme is determined in the following manner.

Fifty μl of a 2.5% solution of fucoidan originating in *Kjellmaniella crassifolia*, 10 μl of this enzyme and 60 μl of a 83 mM phosphate buffer (pH 7.5) containing 667 mM of sodium chloride are mixed together and made to react at 37° C. for 3 hours. Then 105 μl of the reaction mixture is mixed with 2 ml of water under stirring and the absorbance (AT) is measured at 230 nm. As controls, use is made of a reaction mixture prepared by the same method but substituting the enzyme by the above-mentioned buffer alone employed for dissolving the enzyme and another reaction mixture prepared by the same method but substituting the fucoidan solution by water alone and the absorbances (AB1 and AB2) thereof are also measured.

The amount of the enzyme by which one μmol of the glycoside bonds between mannose and uronic acid can be eliminatively cleaved in one minute is taken as one unit (U). The bonds thus cleaved are determined by taking the millimolar molecular extinction coefficient of the unsaturated uronic acid formed in the elimination reaction as 5.5. The activity of the enzyme is determined in accordance with the following equation:

Activity (U/ml)=$(AT-AB1-AB2) \times 2.105 \times 120/(5.5 \times 105 \times 0.01 \times 180)$;

2.105: volume (ml) of the sample the absorbance of which is to be measured;

120: volume (μl) of the enzyme reaction mixture;

5.5: millimolar molecular extinction coefficient (/mM) of unsaturated uronic acid at 230 nm;

105: volume (μl) of the reaction mixture employed for dilution;

0.01: volume (ml) of the enzyme; and

180: reaction time (min).

The protein is determined by measuring the absorbance of the enzyme solution at 280 nm and calculated by taking the absorbance of the 1 mg/ml protein solution as 1.0.

The fucoidan originating from *Kjellmaniella crassifolia* employed as the substrate is prepared in the following manner.

Dry *Kjellmaniella crassifolia* is ground with a free mill Model M-2 (mfd. by Nara Kikai Seisakusho) and treated in 10 times as much 85% methanol at 70° C. for 2 hours. Then it is filtrated and the residue is further treated in 10 times as much methanol at 70° C. for 2 hours. After filtrating, 20 times as much water is added to the residue. Then the mixture is treated at 100° C. for 3 hours and filtrated to thereby give an extract. The salt concentration of the extract is adjusted to the same level as that of a 400 mM solution of sodium chloride. Then cetylpyridinium chloride is added thereto until no more precipitation is formed. After centrifuging, the precipitate is thoroughly washed with ethanol to thereby completely eliminate the cetylpyridinium chloride. Next, it is subjected to desalting and the removal of low-molecular weight substances by using an ultrafiltrater (exclusion molecular weight of ultrafiltration membrane: 100,000, mfd. by Amicon). The precipitate thus formed is eliminated by centrifugation. The supernatant is freeze-dried to thereby give purified *Kjellmaniella crassifolia* fucoidan.

Analysis of the structure of enzyme reaction products:

The above-mentioned endo-fucoidan-lyase is an enzyme which eliminatively degrades the α1→4 bond between D-mannose and D-glucuronic acid in complex polysaccharide. When fucoidan-U obtained above is treated with this enzyme, oligosaccharides having the structures represented by the already-mentioned formulae (I), (II) and (III) are formed.

A portion of each of the above-mentioned three fractions (a), (b) and (c) separated and purified by DEAE-Sepharose FF is pyridyl-(2)-aminated (PA) at the reducing end by using GlycoTAG and GlycoTAG Reagent Kits (both mfd by Takara Shuzo) to thereby give PA saccharides (PA-a), (PA-b) and (PA-c). Those (PA-a), (PA-b) and (PA-c) were analyzed by means of HPLC and the difference from the PA products of three oligosaccharides represented by the formulae (I), (II) and (III) was investigated.

Incidentally, conditions of the HPLC were as follows.

(i) HPLC analysis by using molecular weight fractionation column.
  apparatus: Model L-6200 (mfd. by Hitachi, Ltd.);
  column: SHODEX SB-803 (4.6×250 mm, mfd. by Showa Denko);
  eluent: 0.2 M sodium chloride: dimethyl sulfoxide=9:1;
  detection: Fluorometric Detector F-1150 (mfd. by Hitachi, Ltd.), excitation wavelength: 320 m, fluorescent wavelength: 400 nm;
  flow rate: 1 ml/min.; and
  column temperature: 50° C.

(ii) HPLC analysis with the use of reversed phase column.
  apparatus: Model L-6200 (mfd. by Hitachi, Ltd.);
  column: L-column (4.6×250 mm, mfd. by Kagaku Yakuhin Kensa Kyokai);
  eluent: 50 mM acetic acid-triethylamine (pH 5.5);
  detectin: Fluorometric Detector F-1150 (mfd. by Hitachi, Ltd.), excitation wavelength: 320 nm, fluorescent wavelength: 400 nm;
  flow rate: 1 ml/min; and
  column temperature: 40° C.

As a result of the above-mentioned two HPLC analyses, each of the three oligosaccharides obtained by degrading fucoidan-U with the above endo-fucoidan-lyase was identical with the three oligosaccharides represented by the above formulae (I), (II) and (III), respectively.

Therefore, the compound (a) has a structure wherein unsaturated D-glucuronic acid and L-fucose having a sulfate group bonded thereto are bonded to D-mannose which is the reducing end; the compound (b) has a structure wherein unsaturated D-glucuronic acid and L-fucose having two sulfate groups bonded thereto are bonded to D-mannose which is the reducing end and has a sulfate group bonded thereto; and the compound (c) has a structure wherein D-glucuronic acid and L-fucose having a sulfate group bonded thereto are bonded to D-mannose which is the reducing end, and to this D-glucuronic acid is bonded D-mannose and, in turn, to this D-mannose are further bonded unsaturated D-glucuronic acid and L-fucose having a sulfate group bonded thereto.

As discussed above, the obtained fucoidan-U has a structure wherein D-glucuronic acid and D-mannose are alternately bonded to each other and L-fucose is bonded to at least one D-mannose.

Also, it has a partial structure represented by the following general formula (IV) wherein at least one of alcoholic hydroxyl groups has been sulfated and n stands for an integer of 1 or more.

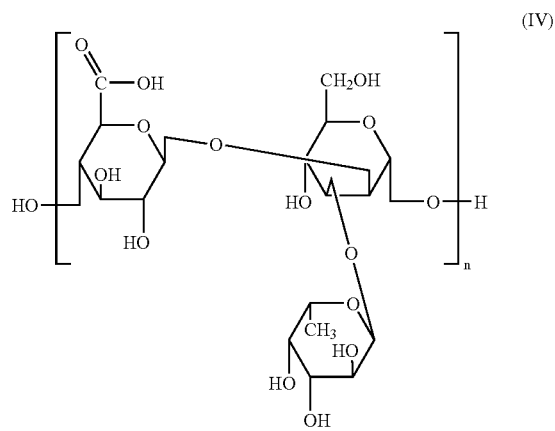

(IV)

Thus, when this fucoidan-U is treated with the above-mentioned endo-fucoidan-lyase, the oligosaccharides represented by the already-mentioned formulae (I), (II) and (III) were produced.

Specific rotation of this freeze-dried fucoidan-U was measured by a high-speed and highly-sensitive polarimeter SEPA-300 (mfd. by Horiba, Ltd.) and found to be −53.6°.

EXAMPLE 5

(1) Preparation of standard fucoidan substance, fucoidan-F and fucoidan U.

Two kg of thoroughly dried *Kjellmaniella crassifolia* was ground with a free mill (mfd. by Nara Kikai Seisakusho). The dry powder thus obtained was suspended in 9 liters of 80% ethanol and treated at 80° C. for 2 hours. Then the mixture was filtrated through a filter paper to thereby give the residue. This residue was repeatedly washed with ethanol and filtered thrice in the same manner as described above to thereby give the residue after ethanol-washing. This residue was suspended in 36 liters of a 0.2 M solution of calcium acetate, treated at 95° C. for 2 hours and filtrated. The residue was washed with 4 liters of a 0.2 M solution of calcium acetate to thereby give 36 liters of an extract containing fucoidan of *Kjellmaniella crassifolia*. To the filtrate thus obtained was added 5% cetylpyridinium chloride until no precipitates were formed any more. Then the precipitates were collected by centrifugation and washed by suspending them in 3 liters of a 0.4 M aqueous solution of sodium chloride followed by centrifugation. After repeating this washing procedure thrice, 1 liter of 4 M aqueous solution of sodium chloride was added to the precipitate and the mixture was stirred. Then ethanol was added thereto so as to give a concentration of 80% and the mixture was stirred and centrifuged to thereby give the precipitate. The obtained precipitate was suspended in 80% ethanol and centrifuged. These procedures were repeated until the absorbance of the supernatant at 260 nm reached zero. The precipitate was dissolved in 3 liters of a 2 M aqueous solution of sodium chloride. After removing the insoluble matters by centrifugation, 100 ml of DEAE-Cellulofine A-800 (mfd. by Seikagaku Kogyo) was added thereto and stirred. Next, the resin added above was removed by filtration. The filtrate was fed into a DEAE-Cellulofine A-800 column equilibrated with a 2 M aqueous solution of sodium chloride and the unadsorbed fraction was subjected to ultrafiltration by using an ultrafiltrater provided with a hollow fiber of exclusion molecular weight of 100,000 or less to thereby completely eliminate the coloring matters and sodium chloride. Next, the insoluble matters were eliminated by centrifugation and filtration followed by freeze-drying to prepare a standard fucoidan substance.

Weight of said standard fucoidan substance was 90 g.

Seven grams of this freeze-dried standard fucoidan substance was weighed out and dissolved in 0.2 M calcium chloride. Then, 4,000 ml of a DEAE-Sepharose FF column was equilibrated with 0.2 M calcium chloride. The standard fucoidan substance dissolved in the 0.2 M calcium chloride was fed into the DEAE-Sepharose FF column and thoroughly washed with 0.2 M calcium chloride. Next, it was developed by linear gradient elution with sodium chloride of 0 to 4 M. Among the fractions thus obtained, those having sodium chloride concentration of 0.05 to 0.8 M were combined, desalted by dialysis and then freeze-dried. Thus 2.1 g of fucoidan-U substantially separated from fucoidan-F was obtained.

Among the fraction eluted above, those having sodium chloride concentration of 0.9 to 1.5 M were combined, desalted by dialysis and then freeze-dried. Thus, 4.7 g of fucoidan-F substantially separated from fucoidan-U was obtained.

Molecular weight of fucoidan-F was determined by means of a gel filtration using Sephacryl S-500 and found to have a molecular weight distribution around about 190,000.

Components of fucoidan-F were analyzed according to a method mentioned in Example 4.

Constituting sugars for fucoidan-F were fucose and galactose and their molar ratio was about 10:1. Uronic acid and other neutral sugars were not substantially contained. Molar ratio of fucose to sulfate was about 1:2.

A 1% fucoidan-F solution (16 ml) was mixed with 8 ml of 32 mU/ml of the above-mentioned endo-fucoidan-lyase solution, 12 ml of 50 mM phosphate buffer (pH 8.0), and 4 ml of 4 M sodium chloride and incubated at 25° C. for 48 hours. No degraded product by the reaction was noted and change of fucoidan-F to low molecule was not noted as well.

Then, specific rotation of this freeze-dried fucoidan-F was measured by a high-speed highly-sensitive polarimeter SEPA-300 (mfd. by Horiba, Ltd.) and found to be −135°.

(2) The freeze-dried fucoidan VI mentioned in Example 1-(3) was used as fucoidan and the degraded product of fucoidan by microorganism was prepared as follows.

Sixty grams of the above freeze-dried fucoidan VI were weighed, dissolved in 20 liters of artificial seawater (mfd. by Jamarin Laboratory), 100 g of peptone and 2 g of yeast extract were added, the mixture was charged in a 30-liter jar fermenter and sterilized, *Flavobacterium* sp. SA-0082 strain (FERM BP-5402) was inoculated and incubation was conducted for 26 hours under the conditions of incubating temperature of 24° C., pH 7, stirring rate of 125 rpm and aeration of 10 liters/minute. The culture medium was centrifuged to remove the cells, treated with an ultrafiltration device equipped with a hollow fiber excluding molecular weight of 30,000 or less to completely remove the low molecular substances and centrifuged and filtrated to remove insoluble matters and the degraded products of fucoidan by the microorganism which were not excluded by a hollow fiber having an excluding molecular weight of 30,000 or less were freeze-dried. Weight of the freeze-dried fucoidan degraded by the microorganism was 32 g.

(3) Freeze-dried fucoidan VI mentioned in Example 1-(3) was subjected to a method mentioned in Example 5-(1) to prepare fucoidan-U and then degraded products of fucoidan-U using endo-fucoidan-lyase was prepared as follows.

Thus, 7 g of above-mentioned freeze-dried fucoidan VI was weighed and dissolved in 0.2 M calcium chloride. Then, 4,000 ml of column of DEAE-Sepharose FF was equilibrated with 0.2 M calcium chloride. After that, the above fucoidan dissolved as such was loaded on a column of DEAE-Sepharose FF, well washed with 0.2 M calcium chloride and eluted with a gradient of 0 to 4 M of sodium chloride. Among the eluted fractions, those where the sodium chloride concentrations were 0.05-0.8 M were collected, desalted by means of dialysis and freeze-dried to give fucoidan-U.

Fucoidan-U (5 g) prepared as such was mixed with 250 ml of a 100 mM Tris-hydrochloride buffer (pH 8.0), 250 ml of 0.8 M sodium chloride and 0.15 ml of an endo-fucoidan-lyase solution (19 U/ml) produced by *Flavobacterium* sp. SA-0082 strain (FERM BP-5402) and made to react at 25° C. for 80 hours.

The reaction mixture was subjected to ultrafiltration using an ultrafiltering apparatus equipped with hollow fiber excluding molecular weight of 3,000 or less and, after the low-molecular substances were completely removed, the insoluble substance were eliminated by means of centrifugation and filtration to collect an enzymatically-degraded fucoidan-U which was not excluded by the hollow fiber having an exclusive molecular weight of 3,000 or less. Said fraction was desalted by a Microacilyzer G3 and freeze-dried to give 2 g of freeze-dried enzymatically-degraded fucoidan-U.

(4) Apoptosis-inducing activity of fucoidan-U and fucoidan-F.

Human promyelocytic leukemia cells HL-60 (ATCC CCL-240) were incubated at 37° C. in an RPMI 1640 medium (mfd. by Gibco) containing 10% of fetal calf serum (mfd. by JRH Bioscience) treated at 56° C. for 30 minutes and then suspended in an ASF 104 medium (mfd. by Ajinomoto Co., Ltd.) in such a manner as to give a concentration of $5 \times 10^4$ cells/900 µl. Then the suspension was pipetted into a six-well plate (mfd. by Falcon) at a ratio of 4.5 ml/well. Each of fucoidan-F and fucoidan-U prepared in Example 5-(1) was dissolved in a 30 mM HEPES buffer (pH 7) containing 120 mM of sodium chloride so as to make the concentration 10 mg/ml followed by subjecting to a treatment in an autoclave at 121° C. for 20 minutes and 100 µl of the resulting one was added to each of the already-prepared suspensions followed incubating at 37° C. in the presence of 5% of carbon dioxide. As a control, only the above buffer was added in the same amount followed by subjecting to the same incubation. Viable cell numbers after 16 hour and 40 hours from initiation of the incubation were counted according to a method mentioned in "Techniques in Tissue Culture" (second edition) (published by Asakura Shuppan, edited by Japan Tissue Culture Society, pages 26-28). Thus, the counting was conducted by a method where dyeing was carried out with Trypan Blue on a hemocytometer.

Figure 5:
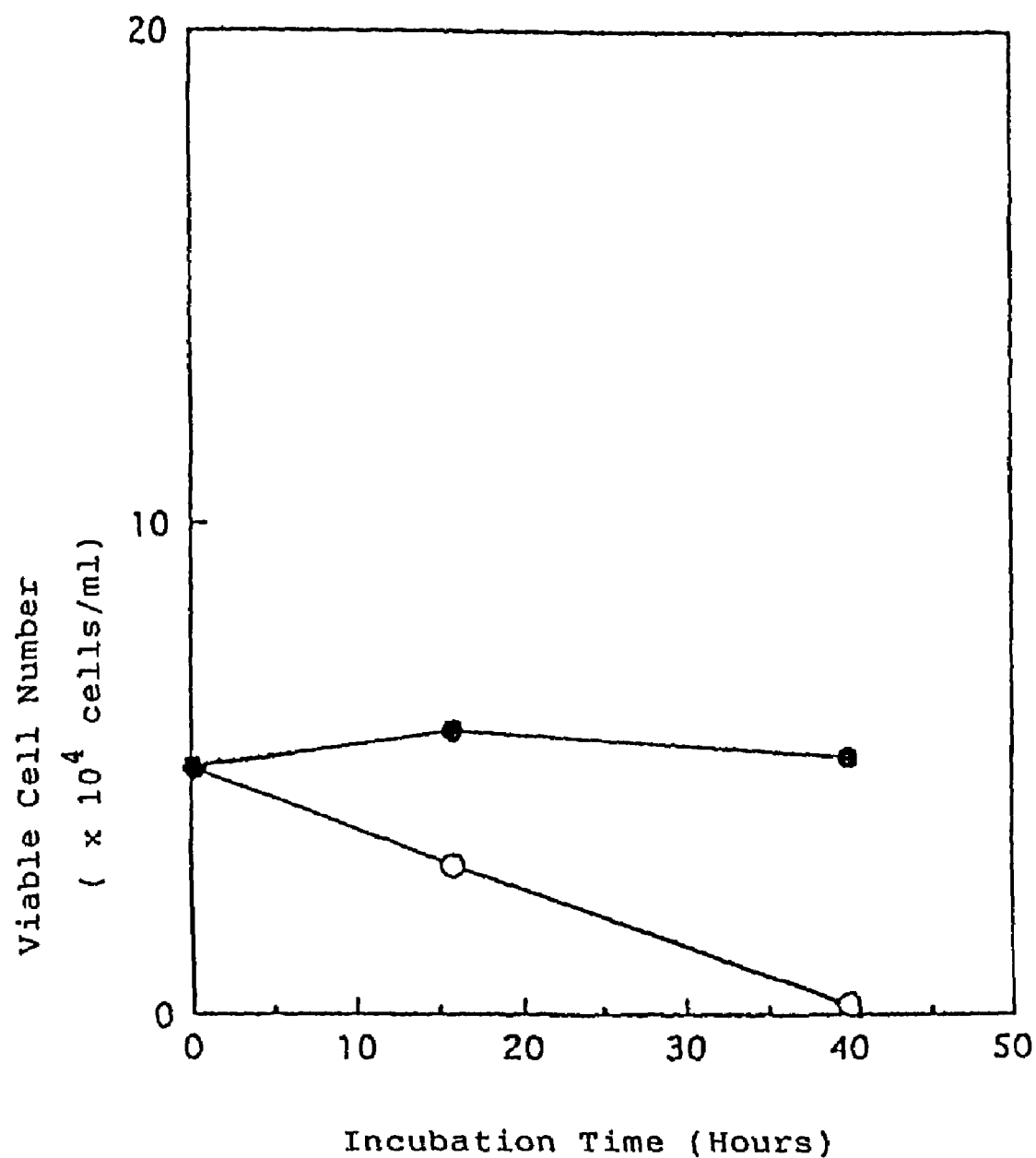
FIG. 5 shows an apoptosis-inducing action of fucoidan-U and fucoidan-F.

The results are given in FIG. 5. Thus, FIG. 5 shows the relation between the incubation time and viable cell numbers in the culture medium when fucoidan-U or fucoidan-F was added to a culture medium of HL-60 cells to make its concentration 1 mg/ml. An abscissa shows incubation time (hours) while an ordinate shows viable cell numbers in the culture medium. With regard to the type of the sulfated fucose-containing polysaccharides, open circles stand for fucoidan-U while black circles stand for fucoidan-F. Incidentally, viable cell numbers in the culture medium of the control (no sample added) after 16 hours and 40 hours from initiation of the incubation were $7 \times 10^4$ cells/ml and $1.4 \times 10^5$ cells/ml, respectively.

As a result, it was found that apoptosis was induced in HL-60 cells by fucoidan-F and fucoidan-U whereupon the rate of proliferation of cells was suppressed.

Each of the fucoidan which was degraded by the microorganism prepared in Example 5-(2) and fucoidan-U which was degraded by enzyme prepared in Example 5-(3) hereinabove was dissolved in a 30 mM HEPES buffer (pH 7) containing 120 mM of sodium chloride to make its concentration 10 mg/ml followed by subjecting to a treatment in an autoclave at 121° C. for 20 minutes and the apoptosis-inducing activity achieved thereby was measured according to the above-mentioned method whereupon the same results as in the case of fucoidan-U shown in FIG. 5 were obtained.

EXAMPLE 6

Green tea was prepared by a conventional method using 10 g of green tea leaves, 0.2 g of vitamin C and 1,000 ml of deionized water. In the product 1 of the present invention, fucoidan II of Example 1 was used and 30 mg of fucoidan per 100 ml of the product was added. In the product 2 of the present invention, a mixture (containing 60% of fucoidan) of fucoidan II of Example 1 and an extract of seaweed with hot water by a conventional method [*Kjellmaniella crassifolia* was extracted with hot water at 95° C. for one hour by a conventional method and the extract was treated with active carbon and freeze-dried (containing 50% of fucoidan); the same material was used in the following Examples as well] was used and added in such an amount that corresponded to 30 mg of fucoidan per 100 ml of the final product. A control was that where nothing was added. An organoleptic test was conducted by 20 panelists by means of a five-step evaluation (where 5 being good while 1 being bad) in terms of feel on tongue, balance of taste, refreshingness of taste and feel on throat and the averages of the results are shown in Table 4.

TABLE 4

| | Organoleptic Evaluations | | |
|---|---|---|---|
| | Product 1 | Product 2 | Control |
| Feel on tongue | | | |
| Mellowness | 4.5 | 3.2 | 2.1 |
| Smoothness | 4.7 | 2.9 | 2.0 |
| Balance of taste | 4.2 | 2.7 | 2.0 |
| Refreshingness of taste | 4.0 | 2.5 | 2.0 |

TABLE 4-continued

| | Organoleptic Evaluations | | |
|---|---|---|---|
| | Product 1 | Product 2 | Control |
| Feel on throat | 4.5 | 3.1 | 2.3 |
| Total evaluation | 4.4 | 2.9 | 2.1 |

From Table 4, the evaluations were that, as compared with the control, the products 1 and 2 of the present invention showed better feel on tongue, better balance and refreshingness of taste, prominent aroma and taste of the tea and excellent balance of taste.

EXAMPLE 7

Nutritive drink was prepared by a conventional method according to a formulation as shown in Table 5.

TABLE 5

| Formulation | |
|---|---|
| Fructose-Glucose-Liquid Sugar | 150 g |
| Purified honey | 2 g |
| Guarana extract | 1 g |
| Korean ginseng extract | 0.1 g |
| Royal jelly | 0.05 g |
| Vitamin C | 0.5 g |
| Nicotinamide | 0.1 g |
| Vitamin $B_1$ hydrochloride | 0.02 g |
| Vitamin $B_6$ hydrochloride | 0.02 g |
| L-Phenylalanine | 0.04 g |
| L-Isoleucine | 0.01 g |
| Citric acid | 1.5 g |
| Perfume | 2 g |
| Deionized water | balance |
| Total | 1,000 ml |

In a product 3 of the present invention, fucoidan-U of Example 4 was used and 40 mg of fucoidan per 100 ml of the final product was added. In a product 4 of the present invention, a mixture (containing 67% of fucoidan) of fucoidan-U of Example 4 and an extract of seaweed with hot water was used and the amount corresponding to 40 mg of fucoidan per 100 ml of the final product was added. The control was that where no fucoidan was added. An organoleptic test was conducted by the same manner as in Example 6. The results are shown in Table 6.

TABLE 6

| | Organoleptic Evaluations | | |
|---|---|---|---|
| | Product 3 | Product 4 | Control |
| Feel on tongue | | | |
| Mellowness | 3.0 | 2.5 | 1.8 |
| Smoothness | 3.5 | 2.4 | 1.5 |
| Balance of taste | 3.6 | 3.2 | 3.0 |
| Refreshingness of taste | 3.8 | 3.0 | 2.8 |
| Feel on throat | 3.7 | 3.4 | 3.0 |
| Total evaluation | 3.4 | 2.9 | 2.4 |

From Table 6, it is noted that the products 3 and 4 of the present invention were quite refreshing beverages having improved feel on tongue, balance of taste, refreshingness of taste and feel on throat as compared with the control.

EXAMPLE 8

Fucoidan drink of a concentrated type was prepared by a conventional method according to a formulation given in Table 7.

TABLE 7

| Formulation | |
|---|---|
| Maltose liquid sugar (kg) | 30.00 |
| Ume (Japanese apricot) powder (kg) | 0.50 |
| ⅕ Transparent lemon juice (kg) | 2.00 |
| Pectin (kg) | 3.00 |
| Citric acid anhydride (kg) | 0.19 |
| Vitamin C (kg) | 0.20 |
| Perfume (kg) | 1.20 |
| Deionized water | balance |
| Total (liter) (pH of the product: 3.1) | 1000 |

The product 5 of the present invention used fucoidan V mentioned in Example 1-(2) and 400 mg of fucoidan per 100 ml of the final product was added. The product 6 of the present invention used a mixture (containing 80% of fucoidan) of fucoidan V and an extract of seaweed with hot water and an amount corresponding to 400 mg of fucoidan per 100 ml of the final product was added. Since the products were drinks of a concentrated type, control 1 where 400 mg of duran gum (a thickener)/100 ml was added and control 2 where 400 mg of xanthan gum/100 ml was added were prepared as controls. They were subjected to an organoleptic test by the same manner as in Example 6 and the results are given in Table 8.

TABLE 8

| | Organoleptic Evaluations | | | |
|---|---|---|---|---|
| | Product 5 | Product 6 | Control 1 | Control 2 |
| Feel on tongue | | | | |
| Mellowness | 4.0 | 3.7 | 3.5 | 3.4 |
| Smoothness | 4.1 | 3.6 | 3.3 | 3.2 |
| Balance of taste | 4.0 | 3.8 | 3.2 | 3.1 |
| Refreshingness of taste | 3.5 | 3.3 | 3.1 | 3.3 |
| Feel on throat | 3.7 | 3.6 | 3.2 | 3.3 |
| Total evaluation | 4.0 | 3.7 | 3.3 | 3.2 |

From Table 8, it is noted that the products 5 and 6 of the present invention showed better feel on tongue and balance of taste as compared with the controls 1 and 2 giving good products having excellent taste as drinks of a concentrated type. Further, fucoidan VI mentioned in Example 1-(3) was used and 400 mg of fucoidan per 100 ml of the product was added to prepare a drink of a concentrated type, which gave the same result. Furthermore, each of the degraded products prepared in Examples 5-(2) and (3) was used and 400 mg of said degraded product per 100 ml of the final product was added to prepare the drinks of the concentrated type, which gave the same result.

EXAMPLE 9

An alcoholic beverage was prepared by a conventional method in accordance with the formulation as shown in Table 9.

TABLE 9

| Formulation | |
|---|---|
| Concentrated juice of frozen Citrus unshu (45 Brix degree) | 110 g |
| Granulated sugar | 80 g |
| Citric acid | 2 g |
| Sodium citrate | 0.5 g |
| Orange essence | 2 g |
| 5% (v/v) aqueous solution of alcohol | balance |
| Total | 1,000 ml |

Note:
The beverage prepared as such was cooled at 5° C. and then carbonic acid was made contained therein by means of a soda siphon.

The product 7 of the present invention used fucoidan II of Example 1 and 35 mg of fucoidan per 100 ml of the final product was added. The product 8 of the present invention used a mixture (containing 55% of fucoidan) of fucoidan II of Example 1 and an extract of seaweed with hot water and the amount corresponding to 35 mg of fucoidan was added. As a control, to which no fucoidan was added was used. An organoleptic test was conducted by the same manner as in Example 6 and the results are given in Table 10.

TABLE 10

| | Organoleptic Evaluations | | |
|---|---|---|---|
| | Product 7 | Product 8 | Control |
| Feel on tongue | | | |
| Mellowness | 4.2 | 3.3 | 2.7 |
| Smoothness | 4.3 | 3.1 | 2.8 |
| Balance of taste | 4.0 | 3.5 | 2.5 |
| Refreshingness of taste | 3.9 | 3.0 | 2.7 |
| Feel on throat | 3.5 | 2.7 | 2.1 |
| Total evaluation | 4.0 | 3.1 | 2.6 |

As shown in Table 10, the products 7 and 8 of the present invention had improved feel on tongue, balance of taste, refreshingness of taste and feel on throat as compared with the control. Particularly in the product 7, acid taste became mild giving a taste of well-ripened mandarin orange.

EXAMPLE 10

A sports drink was prepared by a conventional method according to a formulation of Table 11.

TABLE 11

| Formulation | |
|---|---|
| Glucose | 48 g |
| Fructose | 7.8 g |
| Citric acid | 1.4 g |
| Sodium citrate | 1.0 g |
| Pure salt | 0.3 g |
| Calcium lactate | 0.1 g |
| Magnesium chloride | 0.1 g |
| Vitamin C | 0.2 g |
| Vitamin B1 hydrochloride | 0.02 g |
| Lemon lime perfume | 2 g |
| Deionized water | balance |
| Total | 1,000 g |

In the product 9 of the present invention, fucoidan-U of Example 4 was used and 30 mg of fucoidan per 100 g of the product was added. In the product 10 of the present invention, a mixture (containing 75% of fucoidan) of fucoidan-U of Example 4 and an extract of seaweed with hot water was used and an amount corresponding to 30 mg of fucoidan was added. As a control, to which no fucoidan was added was used. They were subjected to an organoleptic test by the same manner as in Example 6. The results are given in Table 12.

TABLE 12

| | Organoleptic Evaluations | | |
|---|---|---|---|
| | Product 9 | Product 10 | Control |
| Feel on tongue | | | |
| Mellowness | 4.5 | 3.8 | 2.5 |
| Smoothness | 4.3 | 3.5 | 2.3 |
| Balance of taste | 3.9 | 3.5 | 3.2 |
| Refreshingness of taste | 3.7 | 3.2 | 2.9 |
| Feel on throat | 4.0 | 3.5 | 2.8 |
| Total evaluation | 4.0 | 3.5 | 2.7 |

From Table 12, it was noted that, as compared with the control, the products 9 and 10 of the present invention had better feel on tongue, feel on throat and balance of taste, showed excellent balance among the components and gave significant effect of mature taste.

EXAMPLE 11

In order to prepare a plum brandy with fruit, 1,440 g of 75 (w/w) % fructose-glucose-liquid sugar, 670 ml of 95 (v/v) % alcohol and 340 ml of water were mixed in a five-liter bottle equipped with a cap and 1 kg of unripe plum was placed therein.

In the product 11 of the present invention, fucoidan III of Example 2 was used in charging the materials and 40 mg of fucoidan per 100 ml of the final product was used. In the product 12 of the present invention, a mixture (containing 70% of fucoidan) of fucoidan III and an extract of seaweed with hot water and an amount corresponding to 40 mg of fucoidan per 100 ml of the final product as added. A control is that to which no fucoidan was added.

Each bottle was capped and allowed to stand at room temperature for two months with occasional stirring. After that, 1,020 ml of a 28 (v/v) % aqueous alcohol was added thereto and mixed therewith and maturing was continued for two months more to prepare a plum brandy.

Each of the resulting matured plum brandy products was subjected to an organoleptic test by the same manner as in Example 6. The results are given in Table 13.

TABLE 13

| | Organoleptic Evaluations | | |
|---|---|---|---|
| | Product 11 | Product 12 | Control |
| Feel on tongue | | | |
| Mellowness | 4.5 | 3.2 | 2.5 |
| Smoothness | 4.2 | 3.3 | 2.6 |
| Balance of taste | 4.6 | 4.0 | 2.4 |
| Refreshingness of taste | 3.8 | 3.5 | 2.7 |
| Feel on throat | 4.2 | 3.4 | 2.8 |
| Total evaluation | 4.3 | 3.5 | 2.6 |

From Table 13, the products 11 and 12 of the present invention had better feel on tongue and feel on throat as compared with the control and showed mature and well-balanced taste like in the product which was matured for long term.

EXAMPLE 12

In the product 13 of the present invention, homogenized normal milk (containing 88.6 w/v % water, 2.8 w/v % of protein, 3.5 v/w % of fat, 4.5 w/v % of lactose and 0.8 w/v % of ash) and fucoidan I of Example 1 were used and 30 mg of fucoidan per 100 ml of the final product was added. In the product 14 of the present invention, a mixture (containing 80% of fucoidan) of fucoidan I of Example 1 and an extract of seaweed with hot water was used and an amount corresponding to 30 mg of fucoidan was added. The control was that where no fucoidan was added. An organoleptic test was conducted by the same manner as in Example 6 and the results are shown in Table 14.

TABLE 14

Organoleptic Evaluations

|  | Product 13 | Product 14 | Control |
|---|---|---|---|
| Feel on tongue |  |  |  |
| Mellowness | 3.6 | 3.0 | 2.1 |
| Smoothness | 3.5 | 2.9 | 2.5 |
| Balance of taste | 4.0 | 3.6 | 3.0 |
| Refreshingness of taste | 4.2 | 2.8 | 2.4 |
| Feel on throat | 3.9 | 3.3 | 2.1 |
| Total evaluation | 3.8 | 3.1 | 2.4 |

From Table 14, it is noted that, as compared with the control, the products 13 and 14 of the present invention had improved feel on tongue and balance of taste, showed better refreshing of the taste (as compared with the feel in the control as if milk hangs around the tongue; i.e. poor refreshing of the taste) whereupon the resulting milk products can be taken favorably.

EXAMPLE 13

Bean milk was prepared from soybean by a conventional method and coagulated with a coagulator to prepare a common soybean curd.

In the product 15 of the present invention, fucoidan IV of Example 2 was used in the bean milk and an amount of 40 mg of fucoidan per 100 g of the final product was added. In the product 16 of the present invention a mixture (containing 60% of fucoidan) of fucoidan IV of Example 2 and an extract of seaweed with hot water was used and an amount corresponding to 40 mg of fucoidan per 100 ml of the final product was added. A control was that where no additive was used. An organoleptic test was conducted by the same manner as in Example 6. The results are given in Table 15.

TABLE 15

Organoleptic Evaluations

|  | Product 15 | Product 16 | Control |
|---|---|---|---|
| Feel on tongue |  |  |  |
| Mellowness | 4.0 | 3.2 | 2.8 |
| Smoothness | 3.8 | 3.1 | 2.5 |
| Texture | 3.6 | 3.2 | 2.8 |
| Total evaluation | 3.8 | 3.2 | 2.7 |

From Table 15, it is noted that, as compared with the control, the products 15 and 16 of the present invention showed improved feel on tongue and also had a delicate feel on tongue like the soybean cake prepared by compressing with a silk cloth whereby the total feel on eating was significantly improved.

EXAMPLE 14

As to confectionery products, chocolate cream, candy and orange jelly were prepared as follows.

Chocolate cream was prepared by kneading two egg yolks, 125 ml of cowls milk, 10 g of wheat flour and 30 g of sugar with warming.

Candy was prepared as follows. Thus, 1.2 kg of sugar and 0.8 kg of syrup were mixed and dissolved in a dissolver (110° C.), boiled up to 120-1300C by a cooker to make the water content 2% or less and then 16.3 g of lactic acid (a 50% by weight solution), 10.1 g of malic acid, 5.0 g of calcium carbonate and an appropriate amount of perfume were added to prepare the candy.

Orange jelly was prepared as follows. Thus, 9 g of carrageenan was mixed with 180 g of granulated sugar and 800 ml of water was added thereto followed by mixing and dissolving with heating. To this were added 10 g of concentrated fruit juice of unshu-mikan (Citrus unshu), 2 g of citric acid, 1.5 g of sodium citrate, 2 g of orange aroma and 1 g of perfume to give a final product.

In each of the products 17 (chocolate cream), 18 (candy) and 19 (orange jelly) of the present invention, fucoidan-U of Example 4 was used and 20 mg of fucoidan per 100 g of the final product was added. In each of the products 20 (chocolate cream), 21 (candy) and 22 (orange jelly) of the present invention, a mixture (containing 60% of fucoidan) of fucoidan-U of Example 4 and an extract of seaweed with hot water was used and an amount corresponding to 20 mg of fucoidan per 100 g of the final product was added. A control was that where no additive was used. An organoleptic test was conducted and the results are given in Table 16.

TABLE 16

Organoleptic Evaluations

| | Tongue Feel | | | Texture | | | Total Evaln | | |
|---|---|---|---|---|---|---|---|---|---|
| | Products | | | Products | | | Products | | |
| | 17 | 20 | Control | 17 | 20 | Control | 17 | 20 | Control |
| Chocolate Cream | 3.5 | 2.9 | 2.4 | 3.7 | 3.2 | 2.6 | 3.6 | 3.0 | 2.5 |
| | Products | | | Products | | | Products | | |
| | 18 | 21 | Control | 18 | 21 | Control | 18 | 21 | Control |
| Candy | 3.8 | 3.1 | 2.3 | 3.6 | 3.2 | 2.4 | 3.7 | 3.1 | 2.3 |
| | Products | | | Products | | | Products | | |
| | 19 | 22 | Control | 19 | 22 | Control | 19 | 22 | Control |
| Orange Jelly | 4.2 | 3.0 | 2.2 | 4.1 | 2.9 | 2.3 | 4.1 | 2.9 | 2.2 |

From Table 16, it is noted that the products 17/18/19 and 20/21/22 showed improved smoothness in terms of feel on tongue giving a mild feel on eating and exhibited better total evaluations too as compared with controls for each of them.

EXAMPLE 15

As the meat paste product, kamaboko using fish paste and sausage using animal meat were prepared.

In the case of kamaboko, 100 g of water and 20 g of salt were added to 1 kg of ground meat (grade: SA) of walleye pollak, the mixture was disintegrated/kneaded for 15 minutes, 40 g each of it was packed in a vinyl bag, stored overnight at 5° C. and steamed at ordinary pressure to prepare steamed kamaboko (boiled fish paste).

In the case of sausage, 2 kg of pork and 700 g of lard were ground using a plate having pores of 5 mm diameter, then mixed with 7 g of pepper, 3 g of sage and 1 g of mace and the mixture was subjected to cutting and casing using a pig intestine of 2 cm diameter. This is steamed for 15 minutes to prepare sausage.

Fucoidan I of Example 1 was used and 50 mg of fucoidan per 100 g of the product was added to kamaboko (the product 23) prior to disintegrating/kneading or to sausage (the product 24) prior to cutting. In the case of the kamaboko of the product 25 and the sausage of the product 26, a mixture (containing 67% of fucoidan) of fucoidan I of the Example 1 and an extract of seaweed with hot water was used and an amount corresponding to 50 mg of fucoidan per 100 g of the final product was added. A control was that where no additive was used. An organoleptic test was conducted by the same manner as in Example 6 and the results are given in Table 17.

TABLE 17

Organoleptic Evaluations

| | Tongue Feel | | | Texture | | | Total Evaln | | |
|---|---|---|---|---|---|---|---|---|---|
| | Products | | | Products | | | Products | | Con- |
| | 23 | 25 | Control | 23 | 25 | Control | 23 | 25 | trol |
| Kamaboko | 3.8 | 3.4 | 2.7 | 3.7 | 3.0 | 2.6 | 3.7 | 3.2 | 2.6 |
| | Products | | | Products | | | Products | | Con- |
| | 24 | 26 | Control | 24 | 26 | Control | 24 | 26 | trol |
| Sausage | 3.8 | 3.1 | 2.8 | 3.6 | 3.1 | 2.5 | 3.7 | 3.1 | 2.6 |

It is noted from Table 17 that, as compared with the control, the products 23/25 (kamaboko) and 24/26 (sausage) of the present invention showed milder feel on tongue and improved elasticity in texture.

EXAMPLE 16

Ramen (a kind of Chinese noodles) was prepared. Thus, 25.4 g of sodium lactate (50 w/w % solution), 9.4 g of sodium malate and 10 g of calcium carbonate were added to 4 kg of a special flour mixture for ramen (a wheat flour containing a specific alkaline salt), then 1.6 liters of water was further added thereto and the mixture was well mixed up. This was made into noodles using a domestic noodle manufacturing machine (mfd. by Sanyo Electric).

In the product 27 of the present invention, fucoidan II of Example 1 was used and 40 mg of fucoidan per 100 g of the product was added. In the product 28 of the present invention, a mixture (containing 60% of fucoidan) of fucoidan II of Example 1 and an extract of seaweed with hot water was used and an amount corresponding to 40 mg fucoidan per 100 g of the final product was added prior to addition of water. The control was that which contained no additive.

The resulting ramen noodles were cooked by a conventional method and an organoleptic test was conducted for the cooked one by, the same method as in Example 6. The results are given in Table 18.

TABLE 18

Organoleptic Evaluations

| | Product 27 | Product 28 | Control |
|---|---|---|---|
| Feel on tongue | 3.8 | 3.2 | 2.5 |
| Texture | 3.5 | 3.0 | 2.8 |
| Total evaluation | 3.6 | 3.1 | 2.6 |

From Table 18, it is noted that, as compared with the control, the products 27 and 28 of the present invention showed improved feel on tongue and had elastic texture giving a good biting nature by tooth whereby the total evaluation was in a high degree.

EXAMPLE 17

Bread and Chinese manju (dim sum or bun with a filling) were prepared by a conventional method.

Compounding and preparing conditions for the bread and the coating for Chinese manju are given in Tables 19 and 20, respectively.

TABLE 19

Compounding and Preparing Conditions for Bread (Formulation for Sponge Dough Preparation)

| | |
|---|---|
| Wheat flour | 70 parts by weight |
| Yeast | 2 |
| Yeast food | 0.1 |
| Water | 40 |

(Formulation for Final Kneading Operation)

| | |
|---|---|
| Wheat flour | 30 parts by weight |
| Sugar | 5 |
| Salt | 2 |
| Shortening | 5 |
| Casein | 0.5 |
| Water | 25 |

(Preparing Conditions)

| | |
|---|---|
| Fermenting time: | 4 hours (at 27° C. temp and 75% humidity) |
| Proofing time: | 40 minutes (at 38° C. temp and 85% humidity) |
| Baking time: | 35 minutes (at 210° C.) |

TABLE 20

Compounding and Preparing Conditions for Coating of Chinese Manju (Compounding Formulation for the Coating)

| | |
|---|---|
| Wheat flour | 100 parts by weight |
| Sugar | 15 |
| Salt | 0.8 |
| Baking powder | 1 |
| Lard | 5 |
| Yeast | 3.5 |
| Water | 43.5 |

(Preparing Condition)

| | |
|---|---|
| Proofing time: | 90 minutes (at 45° C. temp and 75% humidity) |
| Steaming time: | 15 minutes |

In the products 29 (bread) and 30 (coating for Chinese manju) of the present invention, fucoidan IV of Example 2 was used and 35 mg of fucoidan per 100 g of the bread or of the coating was added. In the products 31 (bread) and 32 (coating for Chinese manju), a mixture (containing 80% of fucoidan) of fucoidan IV of Example 2 and an extract of seaweed with hot water was used and an amount corresponding to 35 mg of fucoidan was added during the compounding stage of the materials. Controls are those where no additive was used.

The resulting bread and coating of Chinese manju were wrapped with a clear-plastic wrap and allowed to stand at 5° C. for 24 hours. An organoleptic test was conducted using the bread and the coating for Chinese manju after allowing to stand as such by the same manner as in Example 6 and the results are as shown in Table 21.

TABLE 21

| | Organoleptic Evaluations | | | | | | | | |
|---|---|---|---|---|---|---|---|---|---|
| | Tongue Feel | | | Texture | | | Total Evaln | | |
| | Products | | | Products | | | Products | | |
| | 29 | 31 | Control | 29 | 31 | Control | 29 | 31 | Control |
| Bread | 3.3 | 2.0 | 1.5 | 3.0 | 1.8 | 1.3 | 3.1 | 1.9 | 1.4 |
| | Products | | | Products | | | Products | | |
| | 30 | 32 | Control | 30 | 32 | Control | 30 | 32 | Control |
| Coating | 2.8 | 2.1 | 1.6 | 3.4 | 1.7 | 1.1 | 3.1 | 1.9 | 1.3 |

When bread and coating for Chinese manju are allowed to stand at low temperature, their moist feels are deteriorated giving a dry feel on eating. As shown in Table 21 however, the products 29/31 and 30/32 of the present invention showed, as compared with the controls for each of them, better feel on tongue and texture after allowing to stand resulting in good inhibition for deterioration in feel on eating whereby a high effect of maintaining their good feel on eating was confirmed.

EXAMPLE 18

In the product 33 of the present invention, a conventionally-prepared sake (Japanese rice wine) and fucoidan-U of Example 4 were used and 25 mg of fucoidan per 100 ml of the final product was added. In the product 34 of the present invention, a mixture (containing 70% of fucoidan) of fucoidan-U of Example 4 and an extract of seaweed with hot water was used and an amount corresponding to 25 mg of fucoidan per 100 ml of the final product was added. A control was that where no additive was used.

An organoleptic test was conducted by the same manner as in Example 6. Taste and aroma were added to the items for the evaluations and the results are given in Table 22.

TABLE 22

| | Organoleptic Evaluations | | |
|---|---|---|---|
| | Product 33 | Product 34 | Control |
| Taste | 3.1 | 3.0 | 3.0 |
| Aroma | 2.9 | 2.8 | 2.9 |
| Feel on tongue | | | |
| Mellowness | 3.9 | 3.2 | 2.5 |
| Smoothness | 4.2 | 3.5 | 2.8 |

TABLE 22-continued

| | Organoleptic Evaluations | | |
|---|---|---|---|
| | Product 33 | Product 34 | Control |
| Balance of taste | 3.5 | 3.1 | 2.9 |
| Refreshingness of taste | 3.6 | 3.2 | 2.7 |
| Feel on throat | 3.8 | 3.0 | 2.6 |
| Total evaluation | 3.7 | 3.1 | 2.8 |

From Table 22, it is noted that, as compared with the control, the products 33 and 34 of the present invention showed better feel on tongue, particularly in terms of smoothness, and exhibited improved refreshingness of taste and feel on throat as well whereby an effect of improving the feel on eating as a luxury has been achieved.

EXAMPLE 19

Conventionally-prepared mirin (a sweet sake) and fermented seasoning were used in this example. Thus, in the products 35 (mirin) and 37 (fermented seasoning) of the present invention, fucoidan III of Example 2 was used and 30 mg of fucoidan per 100 ml of the final product was added. In the products 36 (mirin) and 38 (fermented seasoning), a mixture (containing 67% of fucoidan) of fucoidan III of Example 2 and an extract of seaweed with hot water was used and an amount corresponding to 30 mg of fucoidan per 100 ml of the final product was added. Controls are those where no additive was used.

An organoleptic test was conducted by the same manner as in Example 6. Taste and aroma were added to items for the evaluations and the results are given in Table 23.

TABLE 23

| | Organoleptic Evaluations | | | | | |
|---|---|---|---|---|---|---|
| | Mirin | | | Fermented Seasoning | | |
| | Products | | | Products | | |
| | 35 | 37 | Control | 36 | 38 | Control |
| Taste | 2.9 | 2.8 | 2.8 | 2.7 | 2.6 | 2.7 |
| Aroma | 2.7 | 2.4 | 2.7 | 2.4 | 2.1 | 2.4 |
| Feel on tongue | | | | | | |
| Mellowness | 3.9 | 3.0 | 2.5 | 3.7 | 2.8 | 2.6 |
| Smoothness | 4.1 | 3.2 | 2.7 | 3.8 | 2.9 | 2.4 |
| Balance of taste | 3.4 | 3.2 | 3.1 | 2.9 | 2.5 | 2.4 |
| Refreshingness of taste | 3.5 | 3.1 | 3.0 | 3.2 | 2.8 | 2.3 |
| Total evaluation | 3.4 | 3.0 | 2.8 | 3.1 | 2.6 | 2.5 |

It is noted from Table 23 that, as compared with each of the controls, the mirin products (35/37) and the fermented seasoning product (36/38) of the present invention showed improved feel on tongue (particularly in terms of mellowness and smoothness) and balance of taste whereby the products were effective as seasonings in improving the feel on eating of the materials in cooking.

EXAMPLE 20

Fish powder (4.7 kg), 0.8 kg of dried laver, 2.5 kg of sesame, 1.0 kg of salt and 0.5 kg of sodium glutamate were mixed followed by granulating by a conventional method to prepare furikake (seasoned fish flour).

In the product 39 of the present invention, fucoidan-U of Example 4 was used and 1,000 mg of fucoidan per 100 g of the final product was added. In the product 40 of the present invention, a mixture (containing 60% of fucoidan) of fucoidan-U of Example 4 and an extract of seaweed with hot water was used and an amount corresponding to 1,000 mg of fucoidan per 100 g of the final product was added. The control was that where no additive was used. The product was sprinkled over boiled rice and an organoleptic test on the feel upon eating was conducted by the same manner as in Example 6.

The result was that, as compared with the control, the products 39 and 40 of the present invention well matched with the boiled rice in mouth giving good feel on tongue and showing no coarse feel whereby, as a whole, they were found to improve the quality of the seasoned fish flour.

The food or beverage of the present invention contains a lot of fucoidan having a physiological activity and/or degraded product thereof and, due to an apoptosis-inducing action, etc. of said fucoidan, the product is a healthy or functional food or beverage which shows an effect of preventing the carcinogenesis and suppressing the cancer upon taking it and, particularly, the product is a food or beverage containing functional marine fiber which is useful for maintaining good health of stomach and intestine.

Fucoidan of the present invention, particularly fucoidan from seaweed, is a very good material because it is available at low cost and in large quantities from edible seaweed plants, i.e. edible substance and has a high safety. Moreover, in accordance with the present invention, it is possible to offer fucoidan where the alginic acid content is reduced or eliminated. Said fucoidan is capable of improving feel on eating such as feel on tongue, refreshingness of taste, matching of taste, texture, etc. without deteriorating the inherent good nature of food and beverage and is also capable of maintaining the good nature in view of feel upon eating whereupon it is extremely useful in the manufacture of food and beverage.

What is claimed is:

1. A method for production of food or beverage which contains extract of seaweed consisting of soluble matter in solution of calcium, which comprises:
    (1) preparing the extract of seaweed by adding 10-1000 parts of calcium salt solution to one part of dry seaweed and conducting extraction from the seaweed with said calcium salt solution at 50-130° C., wherein the calcium salt concentration of said calcium salt solution is 25 mM or more;
    (2) recovering soluble matter from the extract prepared in (1);
    (3) freeze-drying soluble matter recovered in (2); and
    (4) adding the soluble matter obtained in (3) to food or beverage, or diluting the soluble matter obtained in (3) with food or beverage, during or after cooking/processing.

2. A method for production of food or beverage which contains extract of seaweed consisting of soluble matter in solution of calcium, which comprises:
    (1) preparing the extract of seaweed by such a manner that extraction from the seaweed is conducted with an alkaline solution and then calcium salt is added to the extract;
    (2) recovering soluble matter from the extract prepared in (1); and
    (3) adding the soluble matter recovered in (2) to food or beverage, or diluting the soluble matter recovered in (2) with food or beverage, during or after cooking/processing.

3. The method for production of food or beverage according to claim 1 or 2 wherein the calcium salt is calcium chloride.

4. The method for production of food or beverage according to claim 1 or 2 wherein the extract of seaweed is derived from Phaeophyceae.

5. The method for production of food or beverage according to claim 1 or 2 wherein the extract of seaweed is derived from *Kjellamaniella crassifolia* or *Laminaria japonica*.

6. A method for production of food or beverage which contains extract of seaweed consisting of soluble matter in solution of calcium, which consists essentially of the steps of:
    (1) preparing the extract of seaweed by adding 10-1000 parts of calcium salt solution to one part of dry seaweed and conducting extraction from the seaweed with said calcium salt solution at 50-130° C., wherein the calcium salt concentration of said calcium salt solution is 25 mM or more;
    (2) recovering soluble matter from the extract prepared in (1);
    (3) freeze-drying soluble matter recovered in (2); and
    (4) adding the soluble matter obtained in (3) to food or beverage, or diluting the soluble matter obtained in (3) with food or beverage, during or after cooking/processing.

7. A method for production of food or beverage which contains extract of seaweed consisting of soluble matter in solution of calcium, which consists essentially of the steps of:
    (1) preparing the extract of seaweed by such a manner that extraction from the seaweed is conducted with an alkaline solution and then calcium salt is added to the extract;
    (2) recovering soluble matter from the extract prepared in (1); and
    (3) adding the soluble matter recovered in (2) to food or beverage, or diluting the soluble matter recovered in (2) with food or beverage, during or after cooking/processing.

* * * * *